US008489408B2

(12) United States Patent
Sawanaga et al.

(10) Patent No.: US 8,489,408 B2
(45) Date of Patent: Jul. 16, 2013

(54) MEDICAL EQUIPMENT MANAGEMENT APPARATUS WHICH PREDICTS FUTURE STATUS OF MEDICAL EQUIPMENT

(75) Inventors: Yuuji Sawanaga, Tochigi (JP); Yoichi Takada, Tochigi-ken (JP); Satoshi Ikeda, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1143 days.

(21) Appl. No.: 10/686,705

(22) Filed: Oct. 17, 2003

(65) Prior Publication Data

US 2004/0138920 A1 Jul. 15, 2004

(30) Foreign Application Priority Data

Oct. 18, 2002 (JP) .................................. 2002-303824
Oct. 3, 2003 (JP) .................................. 2003-346093

(51) Int. Cl.
*G06Q 10/00* (2012.01)
*G06Q 50/00* (2006.01)

(52) U.S. Cl.
USPC ............................................ 705/2; 705/7.11

(58) Field of Classification Search
USPC ........................................................ 705/2–3
See application file for complete search history.

(56) References Cited

U.S. PATENT DOCUMENTS

| | | | | |
|---|---|---|---|---|
| 5,680,025 A * | 10/1997 | Bowers et al. | ................. | 318/806 |
| 5,706,411 A * | 1/1998 | McCormick et al. | ......... | 358/1.14 |
| 5,786,994 A * | 7/1998 | Friz et al. | ........................ | 700/79 |
| 5,874,960 A * | 2/1999 | Mairs et al. | .................... | 715/733 |
| 6,212,256 B1 | 4/2001 | Miesbauer et al. | | |
| 6,381,557 B1 * | 4/2002 | Babula et al. | ................. | 702/183 |
| 6,735,549 B2 * | 5/2004 | Ridolfo | .......................... | 702/181 |
| 6,799,154 B1 * | 9/2004 | Aragones et al. | ............... | 703/22 |
| 6,832,199 B1 * | 12/2004 | Kucek et al. | ...................... | 705/2 |
| 6,970,804 B2 * | 11/2005 | Siegel et al. | .................. | 702/182 |
| 7,032,132 B2 * | 4/2006 | Adachi | ........................... | 714/28 |

FOREIGN PATENT DOCUMENTS

| | | |
|---|---|---|
| JP | 6-261003 | 9/1994 |
| JP | 11-244276 | 9/1999 |
| JP | 2002-149868 | 5/2002 |

OTHER PUBLICATIONS

Ricq, Study of CdTe and CdZnTe detectors for X-ray computed tomography, Nuclear Instruments and Methods in Physics Research Section A: Accelerators,Spectrometers,Detectors and Associated Equipment vol. 458, Issues 1-2, Feb. 1, 2001, pp. 534-543.*

Lie, An Algorithm for Preventive Maintenance Policy, 1986, Reliability, IEEE Transactions on, vol. 35, Issue: 1, pp. 71-75.*

* cited by examiner

*Primary Examiner* — Tran Nguyen
(74) *Attorney, Agent, or Firm* — Oblon, Spivak, McClelland, Maier & Neustadt, L.L.P.

(57) ABSTRACT

A medical equipment management apparatus for managing a medical equipment provided in a medical facility connected to the apparatus through a network. The apparatus comprises a reception unit, a storage unit, a prediction unit, a determination unit, and an informing unit. The reception unit is configured to receive a parameter data regarding the medical equipment more than once. The storage unit is configured to store the parameter data, and the prediction unit is configured to calculate an expectancy of the parameter data to be received in the future based on the stored parameter data. Further, the determination unit is configured to determine a level of the expectancy, and the informing unit is configured to give a notice to the medical facility through the network according to the determined level.

34 Claims, 22 Drawing Sheets

MEDICAL EQUIPMENT MANAGEMENT APPARATUS WHICH PREDICTS FUTURE STATUS OF MEDICAL EQUIPMENT

CROSS-REFERENCE TO RELATED APPLICATION

This application is based upon and claims the benefit of priority from prior Japanese Patent Applications No. P2002-303824, filed on Oct. 18, 2002, and No. P2003-346093, filed on Oct. 3, 2003, the entire contents of which are incorporated herein by reference.

BACKGROUND OF THE INVENTION

1. Field of the Invention

The present invention relates to a medical equipment which monitors a status of the equipment, a medical equipment management apparatus and a method for managing a medical equipment and communicating with a medical facility, and a medical equipment management system including such a medical equipment and such a medical equipment management apparatus.

2. Description of the Related Art

Various types of medical image diagnosis apparatuses are used in medical facilities such as hospitals and the like. One type of such apparatuses is an X-ray computed tomography apparatus (hereinafter referred to as a CT apparatus) which is well known as a medical equipment for obtaining tomographs of a tomography object such as a patient (hereinafter referred to as a specimen). As other types of the medical image diagnosis apparatuses known are, for example, an X-ray diagnosis apparatus, a magnetic resonance imaging apparatus, a nuclear medical imaging apparatus, an ultrasound diagnosis apparatus, and an endoscope apparatus.

These apparatuses are very helpful in a medical diagnosis or treatment. When, however, one apparatus operates during a period when it is difficult to maintain its normal performance during use of the apparatus for the specimen (such use may hereinafter be referred to as an imaging), it results in requiring another imaging for the same specimen. This lowers a throughput of imaging examinations and annoys specimens, from a point of view of a medical facility where the one apparatus is provided. Also from a specimen's point of view, it causes unnecessary X-ray exposure and restraint due to another imaging, and increase of annoyance and anxiety.

In order to avoid those problems mentioned above, a maintenance system has been introduced. For example, as described in a Japanese Patent Application Disclosure P11-244276, a predetermined part of a medical diagnosis apparatus is quantitatively measured periodically and, when a measured value does not meet a predetermined reference value, a warning is displayed. Further, such a status is also automatically reported to a local maintenance provider. Still further, it is also known to the inventors that a future expectancy is predicted based on measured values and an advance response is performed according to a comparison between the future expectancy and a predetermined reference value.

Accordingly, it may be possible to have a maintenance service in advance of it becoming difficult for the medical diagnosis apparatus to maintain its normal performance. This may result in reducing the problems mentioned above.

Although a maintenance service may be implemented according to the comparison with a predetermined reference value, it was not easy, for a hospital staff, a service center, and/or manufacturers of medical diagnosis apparatuses as well as maintenance personnel in the local maintenance provider, to comprehend a current status or situation of the medical diagnosis apparatus. In other words, there was no way of easily and voluntarily knowing when a maintenance service is required; whether maintenance needs may arise earlier due to some reasons other than expected on the basis of experiences or may not arise for the time being; and so on.

In addition, the hospital staff could not easily know that a maintenance service was requested to the local maintenance provider, and details of the request (i.e., when the maintenance service will take place). Therefore, the hospital staff could not have enough time, in some cases, to review and cope with in advance an effect on operations of the medical diagnosis apparatus due to the maintenance service. For example, it may be necessary to change or arrange reservations for CT examinations. On the other hand, for the maintenance personnel, there was not enough time in some cases to arrange a maintenance schedule and to order parts which may be needed in the maintenance service.

SUMMARY OF THE INVENTION

According to a first aspect of the present invention, there is provided a medical equipment management apparatus for managing a medical equipment provided in a medical facility connected to the apparatus through a network. The apparatus includes a reception unit, a storage unit, a prediction unit, a determination unit, and an informing unit. The reception unit is configured to receive a parameter data regarding the medical equipment more than once, and the storage unit is configured to store the parameter data. The prediction unit is configured to calculate an expectancy of the parameter data to be received in the future based on the stored parameter data. Further, the determination unit is configured to determine a level of the expectancy, and the informing unit is configured to give a notice to the medical facility through the network according to the determined level.

According to a second aspect of the present invention, there is provided a medical equipment management apparatus for managing a medical equipment provided in a medical facility connected to the apparatus through a network. The apparatus includes a reception unit, a storage unit, a prediction unit, a determination unit, a second reception unit, and a providing unit. The reception unit is configured to receive a parameter data regarding the medical equipment more than once. The storage unit is configured to store the parameter data. The prediction unit is configured to calculate an expectancy of the parameter data to be received in the future based on the stored parameter data. The determination unit is configured to determine a level of the expectancy, and the second reception unit is configured to receive a reference request for the expectancy from a computer. Further, the providing unit is configured to allow the computer to refer to information of the expectancy based on the received reference request.

According to a third aspect of the present invention, there is provided a medical equipment management apparatus for managing a medical equipment provided in a medical facility connected to the apparatus through a network. The apparatus includes a reception unit, a storage unit, a prediction unit, a determination unit, a second reception unit, and a providing unit. The reception unit is configured to receive a parameter data regarding the medical equipment more than once, and the storage unit is configured to store the parameter data. The prediction unit is configured to calculate an expectancy of the parameter data to be received in the future based on the stored parameter data, and the determination unit is configured to determine a date when the expectancy is substantially identical to a predetermined threshold. Further, the second reception unit is configured to receive a reference request for the date from a computer, and the providing unit is configured to allow the computer to refer to information of the date based on the received reference request.

According to a fourth aspect of the present invention, there is provided a method of managing a medical equipment provided in a medical facility. The method includes the steps of receiving parameter data regarding the medical equipment, storing the parameter data, calculating an expectancy of the parameter data to be received in the future based on the stored parameter data, determining a level of the expectancy, and issuing a notice to the medical facility through the network according to the determined level.

According to a fifth aspect of the present invention, there is provided a method of managing a medical equipment provided in a medical facility. The method includes the steps of receiving parameter data regarding the medical equipment more than once, storing the parameter data, calculating an expectancy of the parameter data to be received in the future based on the stored parameter data, receiving a reference request for the expectancy from a computer, and allowing the computer to refer to information of the expectancy based on the received reference request.

According to a sixth aspect of the present invention, there is provided a method of managing a medical equipment provided in a medical facility. The method includes the steps of receiving a parameter data regarding the medical equipment, storing the parameter data, calculating an expectancy of the parameter data to be received in the future based on the stored parameter data, determining a date when the expectancy is substantially identical to a predetermined threshold, receiving a reference request for the date from a computer, and providing the computer with information of the date based on the received reference request.

According to a seventh aspect of the present invention, there is provided a management system. The system includes a medical facility apparatus and a medical equipment management apparatus. The medical facility apparatus is provided in a medical facility and is configured to transmit parameter data representing a status of a medical equipment through a network. The medical equipment management apparatus is configured to calculate an expectancy of the parameter data of a future based on the parameter data transmitted from the medical facility apparatus, and to determine a level of the expectancy. The medical equipment management apparatus is still further configured to output a notice indicating a situation of the medical equipment according to the determined level.

According to an eighth aspect of the present invention, there is provided a management system. The system includes a medical facility apparatus, a medical equipment management apparatus, and a terminal equipment. The medical facility apparatus is provided in a medical facility and is configured to transmit a parameter data representing a status of a medical equipment through a network. The medical equipment management apparatus is configured to calculate an expectancy of the parameter data of a future based on the parameter data transmitted from the medical facility apparatus, and to transmit information of the expectancy through the network. Further, the terminal equipment is configured to receive and display the information transmitted from the medical equipment management apparatus.

According to a ninth aspect of the present invention, there is provided a monitoring apparatus for managing an equipment connected to the apparatus through a network. The apparatus includes a reception unit, a storage unit, a prediction unit, a determination unit, and an informing unit. The reception unit is configured to receive a data regarding the equipment a plurality of times, and the storage unit is configured to store the data. Further, the prediction unit is configured to calculate an expectancy of the data to be received in the future based on the stored data, and the determination unit is configured to determine a date when the expectancy is substantially identical to a predetermined threshold. The informing unit is configured to give a notice through the network.

According to a ninth aspect of the present invention, there is provided a medical equipment for a use of a medical service. The equipment includes a monitoring device and a correcting device. The monitoring device is configured to monitor a data regarding the medical equipment, and the correcting device is configured to bring the data within a predetermined range when the monitored data is not within the predetermined range.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Embodiments of the present invention will be described with reference to the accompanying drawings. A hospital according to embodiments of the present invention may alternatively be another medical facility including independent physicians and practitioners.

<Configuration>
(First Embodiment)

Figure 1:
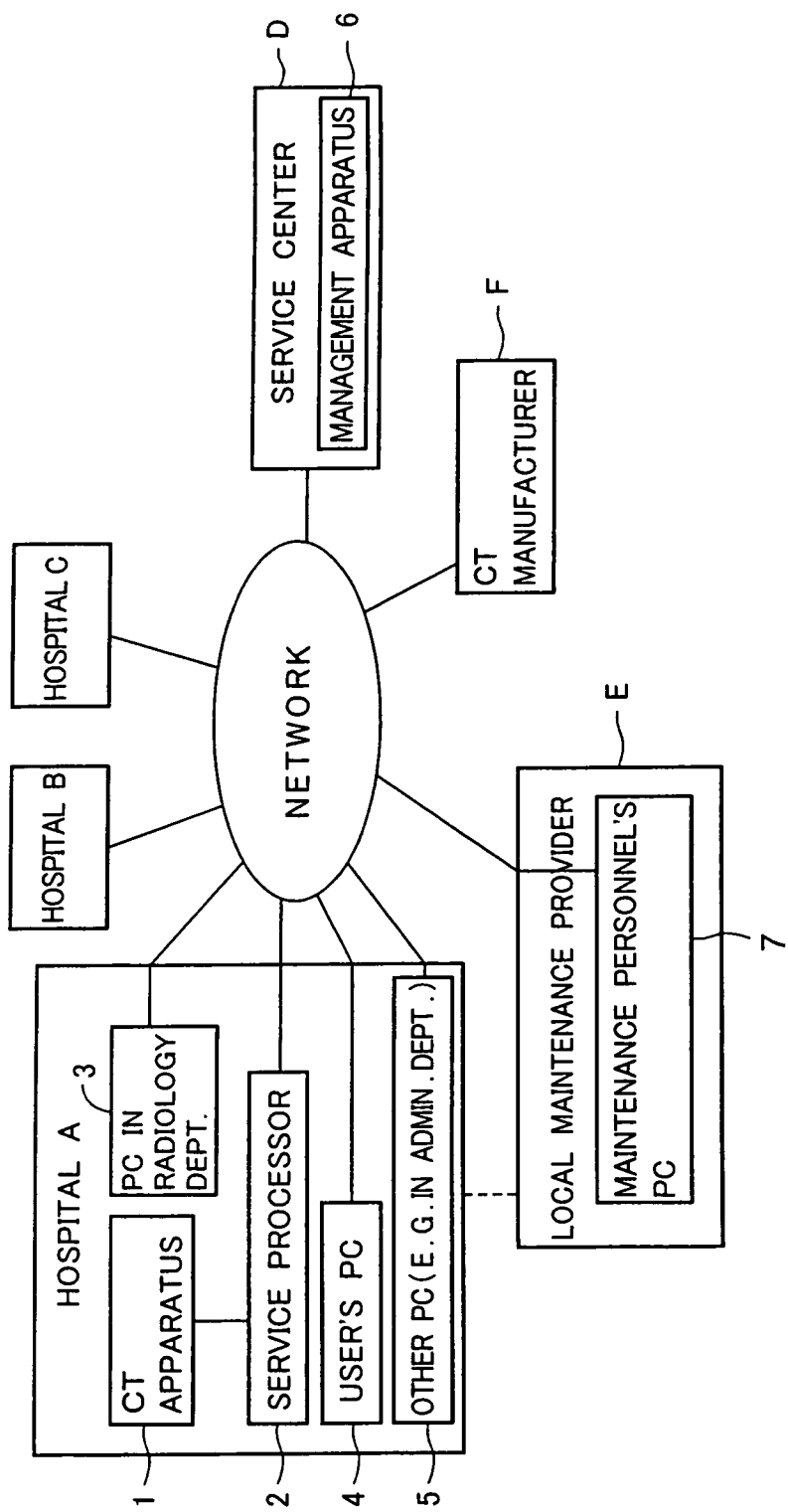
FIG. 1 is an illustration showing an exemplary overview of a medical system including a medical equipment management apparatus according to a first embodiment of the present invention.

FIG. 1 is an illustration showing an exemplary overview of a medical system including a medical equipment management apparatus according to a first embodiment of the present invention. As shown in FIG. 1, hospitals A, B, and C are connected to a service center D through a network. Each of the hospitals A, B, and C includes one or more medical equipments such as the medical diagnosis apparatuses as described in the background of the invention. The service center D monitors the medical equipments provided in the hospitals A, B, and C. Further, a local maintenance provider E is connected to the network. The local maintenance provider E is provided in an area where the hospital A is located. If necessary, a CT manufacturer F may also be connected to the network.

In hospital A, a CT apparatus 1 is provided as the medical equipment. Although only the CT apparatus 1 will be described herein as an example of the equipment, the medical equipment provided in the hospital A may alternatively be any other type of medical equipment including, but not limited to, an X-ray diagnosis apparatus, a magnetic resonance imaging apparatus, a nuclear medical imaging apparatus, an ultrasound diagnosis apparatus, and an endoscope apparatus. There may also be provided other medical equipment in the hospital A. The equipment to be monitored by a service center according to embodiments of the present invention is further not be limited to medical equipment.

The CT apparatus 1 is connected to a service processor 2 which receives information regarding a status of the CT apparatus 1 or regarding each status of one or more parts included in the CT apparatus 1. Such information is hereinafter referred to as a parameter data. The service processor 2 provides the service center D with the parameter data through the network.

The hospital A further includes PCs (personal computers) 3 to 5. The PC 3 is provided in a department of radiology in the hospital A and may be used by radiological technologists. The PC 4 is a PC which is usually used by a user in the hospital A. The 'user' may include a doctor, the radiological technologist, a system administrator, and other users. There is another PC 5 in the hospital A. The PC 5 may be provided, but not limited to, for example, in an administration department. The PC 5 may be provided in a department regarding management, operation, maintenance of the CT apparatus 1 in the hospital A. Further, the number of each PC 3 to 5 may be more than one. The PCs 3 to 5 can receive emails from the service center D and can allow the radiological technologist, the user, and the like to access to information provided in the Internet web site by the service center D, through a WWW (World Wide Web) browser. The information may be expectancy based on monitored parameter data of the CT apparatus 1 or information provided in response to a reference request. The reference request will be described in detail later.

One example of the parameter data is amplification characteristic, such as a bias voltage level and an amplitude voltage level of an amplifier. The amplifier is, for example, used for amplifying electric signals which is converted from optical signals transmitted between a rotation part and a fixed part of a gantry of the CT apparatus 1. Such an example of the amplifier will be described in detail later.

The hospitals B and C may include components similar to the hospital A.

Any one or more of PCs, including the PCs 3 to 5, which are described in embodiments of the present invention, may alternatively be other types of computers.

When it comes to the service center D, a medical equipment management apparatus 6 is provided for monitoring and managing information or a status of the CT apparatus 1 in the hospital A and other medical equipment which are provided in the hospitals A, B, and/or C. In addition, a maintenance service is directed or requested from the service center D to the local maintenance provider E. Details of the medical equipment management apparatus 6 will be described later.

The local maintenance provider E provides hospitals including the hospital A in an area assigned to the local maintenance provider E with a maintenance service and any other necessary assistance locally. There is a PC 7 in the local maintenance provider E. The PC 7 is a maintenance personnel's PC or a PC which is used for managing information of the hospital A.

Similar to the PCs 3 to 5, the PC 7 can also receive emails from the service center D and can allow its user to access to information provided in the Internet web site by the service center D, through a WWW browser. The information may be expectancy based on monitored parameter data of the CT apparatus 1 or information provided in response to a reference request. The reference request will be described in detail later.

Further, medical equipment manufacturers may also be connected to the network. In the first embodiment of the present invention, the CT manufacturer F which has manufactured the CT apparatus 1 can be connected to one or more of the hospital A, the service center D, and the local maintenance provider E through the network so that CT engineers are given a chance to find and analyze technical problems, if occurred, as soon as possible. This leads to the CT engineers' early investigation of a solution to the problems based on the analysis.

Figure 2:
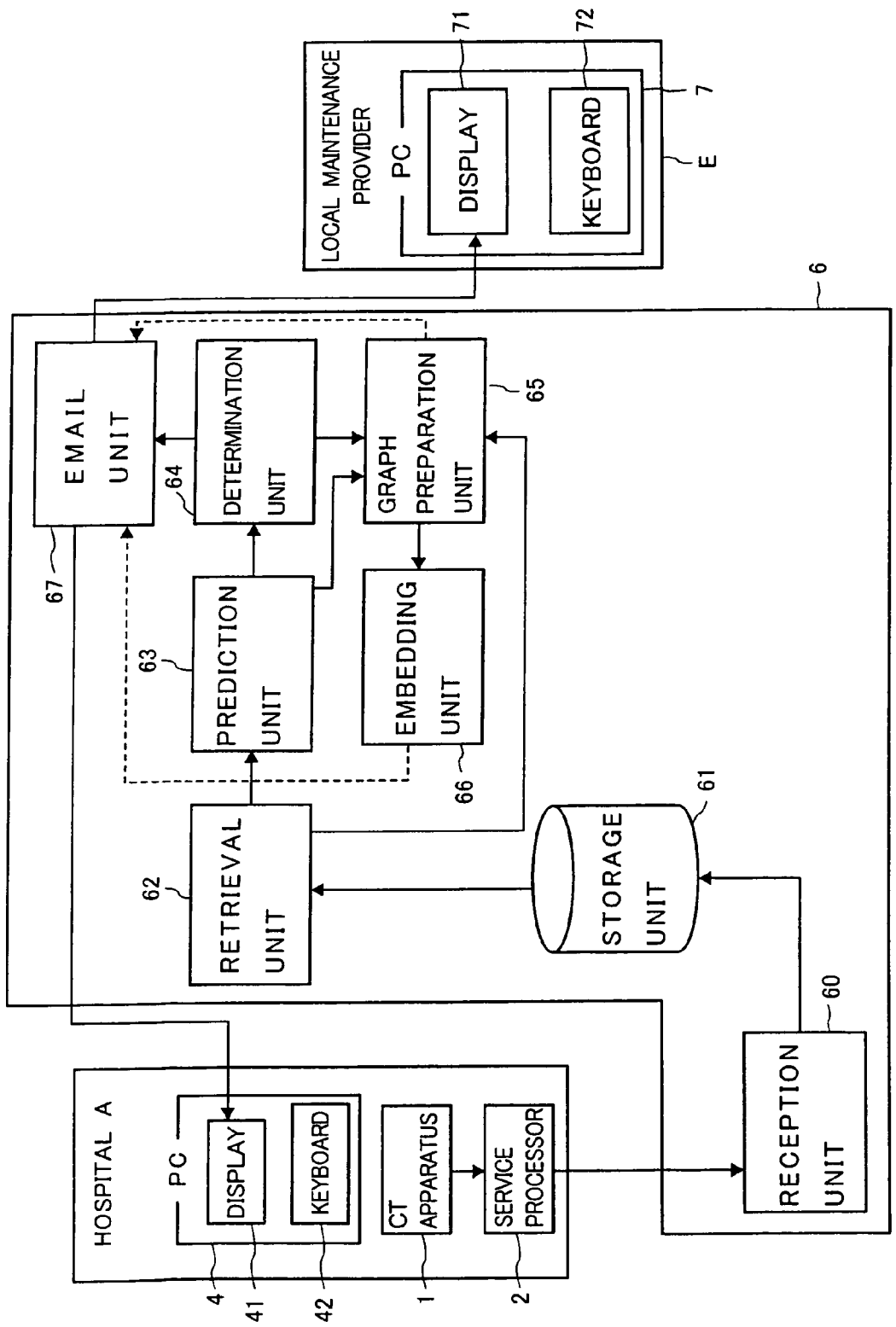
FIG. 2 is a block diagram showing a first exemplary configuration of the medical equipment management apparatus in relationship to a hospital and a local maintenance provider according to the first embodiment of the present invention.

Next, a further detailed explanation will be made with respect to a relationship among the hospital A, the medical equipment management apparatus 6, and the local maintenance provider E. FIG. 2 is a block diagram showing a first exemplary configuration of the medical equipment management apparatus 6 in relationship to the hospital A and the local maintenance provider E according to the first embodiment of the present invention.

The medical equipment management apparatus 6 provided in the service center 6 includes a reception unit 60, a storage unit 61, and a retrieval unit 62. The reception unit 60, as an FTP server, for example, receives parameter data from the hospital A. The storage unit 61, as a data mart, for example, stores the parameter data received by the reception unit 60. The retrieval unit 62 reads out (or retrieves) the parameter data stored in the storage unit 61 as prior data.

In addition, the medical equipment management apparatus 6 includes a prediction unit 63, a determination unit 64, a graph preparation unit 65, and an embedding unit 66. The prediction unit 63 predicts expectancy of parameter data to be received in the future from the hospital A by calculation based on the prior parameter data read out by the retrieval unit 62. The determination unit 64 compares the expectancy to a predetermined threshold, and determines whether or not the expectancy exceeds the predetermined threshold. The determination unit 64 may also or alternatively determine (predict) a date when the expectancy will exceed (or be equal to) the predetermined threshold. Such a date is hereinafter referred to as a probable date. The graph preparation unit 65 prepares a graph showing the prior parameter data and the expectancy based on the prediction or based on the prediction and the determination. If necessary, the embedding unit 66 embeds the prepared graph in reports which are provided to the hospital A and/or the local maintenance provider E.

Further, the medical equipment management apparatus 6 still includes an email unit 67. The email unit 67 transmits emails to the local maintenance provider E and the hospital A, if necessary, according to the determination by the determination unit 64. The emails may include an content based on the determination.

Operations of the medical equipment management apparatus 6 configured as described above will be described below in relationship to operations in the hospital A and the local maintenance provider E.

In the hospital A, specimens are examined by the CT apparatus 1. The service processor 2 receives parameter data from the CT apparatus 1 regularly, at any or given time, or in response to a predetermined trigger event. The service processor 2 then provides the reception unit 60 with the received parameter data regularly, at any or given time, or every time when the service processor 2 receives the parameter data from the CT apparatus 1. Further, the service processor 2 may alternatively provide the reception unit 60 with the parameter data in response to requests from the medical equipment management apparatus 6. Except for a case of providing every time when the service processor 2 receives the parameter data from the CT apparatus 1, the service processor 2 may provide all parameter data received from the CT apparatus 1 since the previous providing by the service processor 2. Alternatively, only a part or a latest of parameter data already received from the CT apparatus 1 may be provided to the reception unit 60.

In any case, parameter data provided by the service processor 2 are received by the reception unit 60 through, for example, exclusive lines. The received parameter data are stored in the storage unit 61 and used for expectancy calculation in a later stage. Prior to the storage, the reception unit 60 sorts the received parameter data in accordance with parts or the like regarding the parameter data. The parameter data and the following parameter data to be received may be stored in tables each of which is provided for each part or the like of the CT apparatus 1.

The reception unit 60 is not limited to on-line reception of the parameter data. For example, the service center D may regularly receive storage media storing parameter data from the hospital A directly or through the local maintenance provider E. The storage media may be placed in a readout system (the reception unit 60) by an operator, and the parameter data stored in the media may be received by the reception unit 60.

Parameter data stored in the storage unit 61 are retrieved by the retrieval unit 62 regularly or at any or given time. The parameter data may be alternatively retrieved in response to reference requests from PCs 3-5, 7 and the like which will be described later. In the retrieval, the retrieval unit 62 may retrieve parameter data for all parts of the CT apparatus 1. Alternatively, the retrieval unit 62 may select one or more specific parts and retrieve parameter data only for such selected parts.

Further, parameter data retrieved regarding each part of the CT apparatus 1 may be all parameter data of the part or may alternatively be specific parameter data obtained or received every predetermined interval. Still alternatively retrieved may be only latest parameter data at the instant of retrieval.

The retrieved parameter data (prior data) are provided to the prediction unit 63. In the prediction unit 63, expectancy of parameter data to be received in the future is predicted by calculation based on the parameter data (prior data) retrieved from the storage unit 61. When all parameters stored in the storage unit 61 have been retrieved for the prediction, the expectancy will have a higher degree of accuracy. The future may be a time in a predetermined period, such as, for example, a week or a month, from the time of prediction. When the expectancy is predicted in response to reference requests, the future may be a time indicated in the requests, if indicated.

When a transition of parameter data regarding a part of the CT apparatus 1, which was prepared in a previous prediction, is stored, a present prediction may be implemented based on the transition and newly received and retrieved parameter data. In this case, there may be a possibility that a predicted expectancy has a lower degree of accuracy, compared to a case using more or all received parameter data. However, it may also be possible to predict the expectancy more easily and more quickly.

In some cases, a transition of parameter data regarding an old part, before being replaced with a current one, of the CT apparatus 1 may still be stored in the storage unit 61 or other unit. In such a case, the transition regarding the old part may be considered for predicting expectancy of parameter data regarding the current part. The transition may alternatively be used as correction data for correcting expectancy predicted based on received parameter data regarding the current part.

A further possible way of prediction is applicable to the following case. It may not be so rare that a part which is similar to or has the same model number as what is used in the CT apparatus 1 is being used or was used in a CT apparatus or other type of apparatus provided in the hospital A or in other hospitals. If a transition of parameters regarding such a part is obtained in the service center D, such an obtained transition may be considered for predicting an expectancy of parameter data regarding the part used in the CT apparatus 1. The transition may alternatively be used as correction data for correcting an expectancy predicted based on received parameter data regarding the part used in the CT apparatus 1.

It does not matter whether a prediction engine used in the prediction unit 63 is linear or nonlinear. A data mining technique is one exemplary technique for the prediction. In the data mining technique, there may be used, for example, a co-occurrence relation analysis technique (or a basket analysis), a classification technique (or a decision tree), and/or a neural network. In addition, an expectancy may be analogized by extracting pattern information from received parameter data. Another prediction may use differential information between a plurality of parameter data.

Turning back to FIG. 2, when an expectancy has been obtained in a manner as described above, the expectancy is compared to a predetermined threshold and is determined whether or not the expectancy exceeds the predetermined threshold in the determination unit 64. The determination unit 64 holds thresholds corresponding to parameters, respectively. The threshold is a type of indicator for determining whether or not it shows that a part regarding parameter data deteriorates so as not to operate properly or is becoming unable to maintain its normal operation. Two thresholds may be set for one expectancy. One is an upper threshold showing an upper limitation for maintaining a part to operate properly. Another is a bottom threshold showing a bottom limitation for maintaining the same part to operate properly.

In addition, whether or not there are two thresholds described above, a predetermined threshold can be dual. That is, for example, a standard level and a dangerous level can be set for each predetermined threshold. A dangerous threshold level indicates an emergency situation that it is nearly impossible for the part to properly operate, i.e., it is necessary to repair or replace the part immediately. Therefore, it requires an urgent contact with the local maintenance provider E. On the other hand, a standard threshold level may be set at a 70 percent of the dangerous threshold level, for example. The standard threshold level does not indicate an emergency situation as the dangerous threshold level, but it indicates maintenance service will be required in the near future. It may also be necessary to decide whether to wait for a next regular maintenance service or to ask for a maintenance service before the next regular maintenance service, in consideration of a time of the next regular maintenance service.

The determination unit 64 also or alternatively determines a probable date when an expectancy exceeds the threshold (the standard threshold level or the dangerous threshold level) based on the prediction in the prediction unit 63 when the probable date is requested from one or more PCs 3-5, 7, and the like.

Further, the graph preparation unit 65 prepares a graph showing parameter data stored in the storage unit 61 and a predicted expectancy. The prepared graph may reflect a determination result in the determination unit 64. Further, a function which becomes a base of the prediction in the prediction unit 63 may also be expressed in the graph. Instead of or in addition to the graph preparation, the graph preparation unit 65 may prepare a table including the parameter data and the predicted expectancy.

The prepared graph is embedded or included in a report in the embedding unit 66. The report may be, for example, a so-called performance report including operation conditions of the CT apparatus 1. An alternative example of the report may be a so-called QA (quality assurance) report including qualities such as an image quality obtained regarding the CT apparatus 1. These reports are usually provided to the hospital A and/or the local maintenance provider E regularly, in the event of an emergency, and/or in response to requests. Therefore, the prepared graph (the predicted expectancy) can also be provided to the hospital A and/or the local maintenance provider E regularly, in the event of an emergency, and/or in response to requests.

When an expectancy is determined to exceed the threshold (the standard threshold level or the dangerous threshold level) in the determination unit 64, the email unit 67 transmits email(s) to issue a notice of such an occurrence, the expectancy, the probable date, the graph, and/or the report. The expectancy, the probable date, the graph, and/or the report may be accessed by clicking a URL written in the email, and accordingly referred through the WWW browser. In addition, the email is transmitted to the PC 7 provided in the local maintenance provider E for the purpose of giving a notice of a request of a maintenance service. The email is also transmitted to the PC 4 and maybe also the PCs 3 and 5 in the hospital A for the purpose of giving a notice of letting the user recognize a current status of the CT apparatus 1 and immediate or near future's necessity of a maintenance service. The email to the hospital A may be a CC (carbon copy) of the email transmitted to the local maintenance provider E.

When the email is received in the PC 7, the email can be displayed in a display 71 of the PC 7 and referred by maintenance personnel or the like. Accordingly, it becomes possible for the local maintenance provider E to study a time for a maintenance service based on the determination (i.e., information included in the received email). A study result may lead to an arrangement of repairs, parts replacement, and so on. Information to be written in and/or to be attached with the email may be different according to the determination of whether or not the expectancy exceeds the threshold (also whether the expectancy is between the standard threshold level and the dangerous threshold level or exceeds the dangerous threshold level).

When the email is received in the PC 4, the email can be displayed in a display 41 of the PC 4 and referred to by the user. Accordingly, it becomes possible for the user to recognize the necessity of having a maintenance service on the CT apparatus 1 immediately or in the near future. Based on the information obtained through the email, the user can take actions in advance for operations without the CT apparatus 1 for a maintenance period. The email may also be transmitted to the PC 3 and 5. This makes it possible to let other hospital staff relating to operations of the CT apparatus 1 recognize the same, for example. Information to be written in and/or to be attached with the email may be the same as or be different from that for the PC 7 provided in the local maintenance provider E.

By receiving the email, the hospital A can spontaneously contact the local maintenance provider E and discuss a maintenance service with maintenance personnel.

Further, the PC 4 includes a keyboard 42 for various operations, such as, for example, input, designation, and request. The PC 7 also includes a keyboard 72 for various operations, such as, for example, input, designation, and request.

(Second Embodiment)

Figure 3:
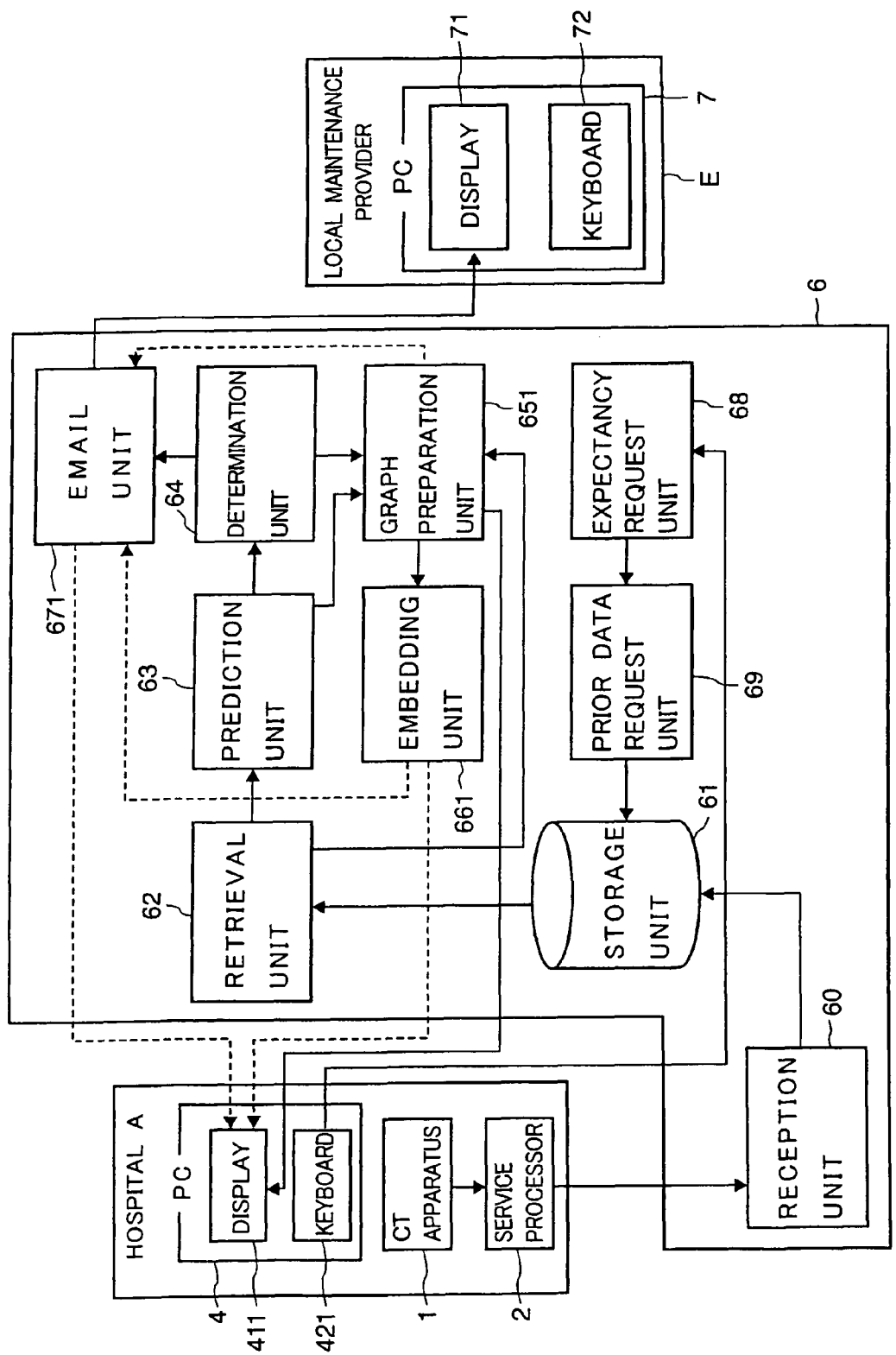
FIG. 3 is a block diagram showing a second exemplary configuration of the medical equipment management apparatus in relationship to the hospital and the local maintenance provider according to a second embodiment of the present invention.

Another relationship among the hospital A, the medical equipment management apparatus 6, and the local maintenance provider E will be described with reference to FIG. 3. FIG. 3 is a block diagram showing a second exemplary configuration of the medical equipment management apparatus 6 in relationship to the hospital A and the local maintenance provider E according to a second embodiment of the present invention.

In FIG. 3, components, which operate in a manner similar to the components shown in FIG. 2 are given the same reference numbers and are detailed explanations of their components are appropriately omitted. In addition, operations of the medical equipment management apparatus 6 are similar to those described in the first embodiment except for those described below. Therefore, detailed explanations of such operations similar to those in the first embodiment are omitted.

The medical equipment management apparatus 6 further includes an expectancy request unit 68 and a prior data request unit 69. The expectancy request unit 68 requests plotting an expectancy in response to reference requests of the expectancy of parameter data from the hospital A. The prior data request unit 69 requests prior data (i.e., parameter data) towards a storage unit 611 in response to the requests from the expectancy request unit 68.

When the user operates a keyboard 421 of the PC 4 so as to request an expectancy of parameter data regarding a specific part or the like of the CT apparatus 1, this request is sent to the expectancy request unit 68. One possible way of sending the request from the keyboard 421 may be inputs, selection, and/or button pressing in a web site of the service center D through a WWW browser. Another example may be using email instead of the WWW browser. The request may correspond to a probable date, instead of the expectancy.

Such a request of the expectancy or the probable date may alternatively be made by a radiological technologist through the PC 3 or by other hospital staff in a department of administration or else through the PC 5.

When the request from the PC 4 (3, or 5) is received by the expectancy request unit 68 through the network, the expectancy request unit 68 sends a request to the prior data request unit 69 according to a content of the request from the PC 4 (3, or 5). The request to the prior data request unit 69 may be a graph showing prior data (parameter data) and an expectancy. In another exemplary case, it may be an embedding of the graph into a report, such as, for example, a performance report and a QA report.

The prior data request unit 69 requests the storage unit 611 parameter data necessary for the request from the expectancy request unit 68. The storage unit 611 provides the retrieval unit 62 with parameter data meeting the request from the prior data request unit 69.

The parameter data provided to the retrieval unit 62 are used for calculations in the prediction unit 63 so as to predict an expectancy. In the prediction unit 63 and the determination unit 64, operations described before are implemented. The graph preparation unit 651 and the embedding unit 661 implement operations similar to those in FIG. 2. When the request from the hospital A regards a graph, the graph prepared in the graph preparation unit 651 is available in the PC 4 (3, or 5) which has made the request. In such a PC 4 (3, or 5), the graph can be referred in the display 411 (or the like). Also when the request from the hospital A corresponds to a report, the report embedded with the graph is available in the PC 4 (3, or 5) which has made the request. In such a PC 4 (3, or 5), the report can be referred in the display 411 (or the like).

This reference may be realized through the WWW browser, by operating buttons or inputting necessary information. Alternatively, the reference may be made through email from the medical equipment management apparatus 6. If the email includes a URL for accessing to the graph or the report, the user or other hospital staff can refer to the graph or the report through the Internet web site by clicking the URL. If the email is attached with a file including the graph or the report, the user or other hospital staff can open the attached file and refer to the graph or the report.

According to the second embodiment of the present invention, the user or other hospital staff can request information regarding an expectancy for himself or herself. Therefore, anytime he or she feels it necessary, even when he or she feels anxiety, he or she can obtain an expectancy, the graph, and/or the report to see a current situation without waiting for a notice by email from the medical equipment management apparatus 6. This leads to relief of anxiety. In addition, the hospital A can study or take appropriate actions for responding to the situation in advance of receiving the email, depending on a result of the reference.

(Third Embodiment)

Requests from the hospital A has been described in the second embodiment of the present invention. Such requests may also be made from the local maintenance provider E.

Figure 4:
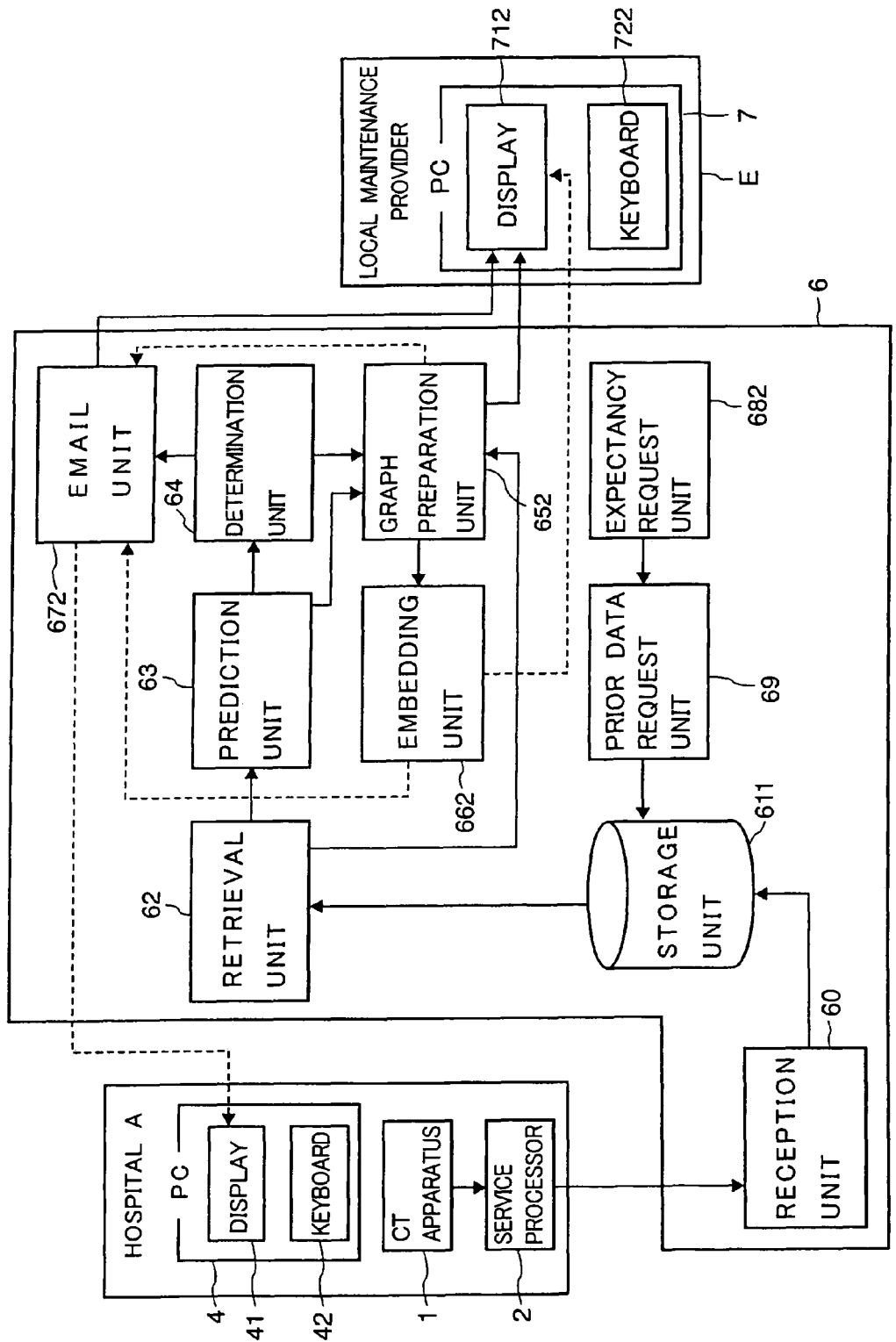
FIG. 4 is a block diagram showing a third exemplary configuration of the medical equipment management apparatus in relationship to the hospital and the local maintenance provider according to a third embodiment of the present invention.

FIG. 4 is a block diagram showing a third exemplary configuration of the medical equipment management apparatus 6 in relationship to the hospital A and the local maintenance provider E according to a third embodiment of the present invention.

In FIG. 4, components, which operate in a manner similar to the components shown in FIG. 2 or 3 are given the same reference numbers and detailed explanations are appropriately omitted. In addition, operations of the medical equipment management apparatus 6 are similar to those described in the first or second embodiment except for those described below. Therefore, detailed explanations of such operations similar to those in the first or second embodiment are omitted.

When the maintenance personnel or other staff in the local maintenance provider E operates a keyboard 722 of the PC 7 so as to request an expectancy of parameter data regarding a specific part or the like of the CT apparatus 1, this request is sent to the expectancy request unit 682. The request from the keyboard 722 may be made as in the case of the keyboard 421 described in the second embodiment.

When the request from the PC 7 is received by the expectancy request unit 682 through the network, the expectancy request unit 682 sends a request to the prior data request unit 69 according to a content of the request from the PC 7. The request to the prior data request unit 69 may be as described in the second embodiment. Subsequently, the graph and/or the report are obtained as described in the second embodiment.

When the request from the local maintenance provider E corresponds to a graph, the graph prepared in a graph preparation unit 652 is available in the PC 7 which has made the request. In such a PC 7, the graph can be referred in the display 712. Also when the request from the local maintenance provider E corresponds to a report, the report embedded with the graph by an embedding unit 662 is available in the PC 7 which has made the request. In such a PC 7, the report can be referred in a display 712. This reference may be realized in various manners as described in the second embodiment.

According to the third embodiment of the present invention, the maintenance personnel or the other staff can request information regarding an expectancy for himself or herself. Therefore, anytime he or she feels it necessary, for example, when he or she wants to identify the situation of the CT apparatus 1 or to arrange parts in sufficient time, he or she can obtain an expectancy, the graph, and/or the report to see a current situation without waiting for a notice by email from an email unit 672 of the medical equipment management apparatus 6. In addition, the local maintenance provider E can coordinate schedules for maintenance personnel and/or arrange (or order) some parts for replacement in advance of receiving the email, depending on a result of the reference.

(Fourth Embodiment)

The above mentioned requests may also be made from inside the service center D.

Figure 5:
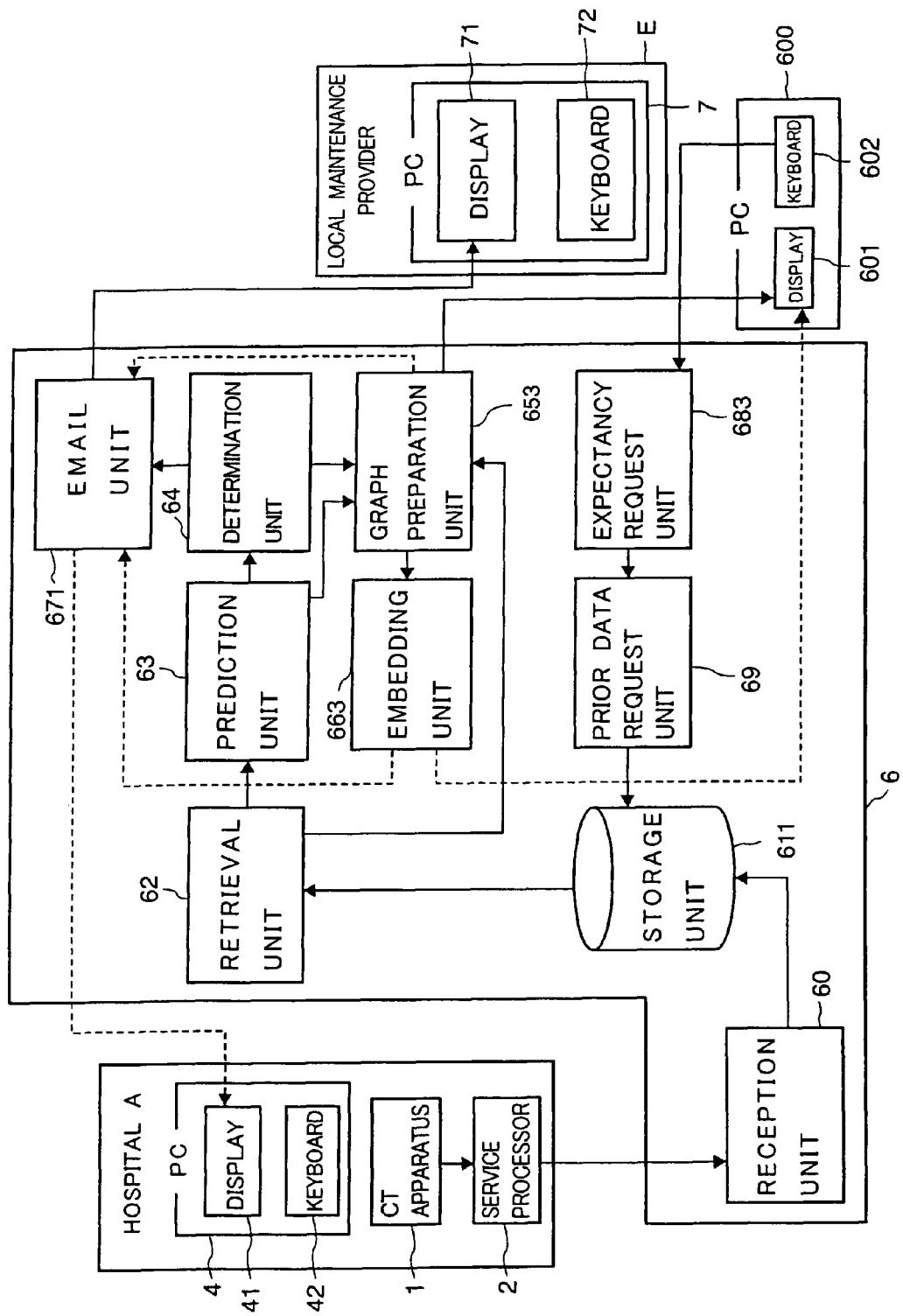
FIG. 5 is a block diagram showing a fourth exemplary configuration of the medical equipment management apparatus in relationship to the hospital and the local maintenance provider according to a fourth embodiment of the present invention.

FIG. 5 is a block diagram showing a fourth exemplary configuration of the medical equipment management apparatus 6 in relationship to the hospital A and the local maintenance provider E according to a fourth embodiment of the present invention.

In FIG. 5, components, which operate in a manner similar to the components shown in FIG. 2 or 3 are given the same reference numbers and detailed explanations are appropriately omitted. In addition, operations of the medical equipment management apparatus 6 are similar to those described in the first or second embodiment except for those described below. Therefore, detailed explanations of such operations similar to those in the first or second embodiment are omitted.

When a person in the service center D, who has or may not have an access authority to the medical equipment management apparatus 6, operates a keyboard 602 of a PC 600 provided in the service center D so as to request an expectancy of parameter data regarding a specific part or the like of the CT apparatus 1, this request is sent to an expectancy request unit 683. The request from the keyboard 602 may be made as in the case of the keyboard 421 described in the second embodiment.

When the request from the PC 600 is received by the expectancy request unit 683 through the network, the expectancy request unit 683 sends a request to the prior data request unit 69 according to a content of the request from the PC 600. The request to the prior data request unit 69 may be as described in the second embodiment. Subsequently, the graph and/or the report are obtained as described in the second embodiment.

When the request from inside the service center D corresponds to a graph, the graph prepared in a graph preparation unit 653 is available in the PC 600 which has made the request. In such a PC 600, the graph can be referred in a display 601. Also when the request from inside the service center D regards a report, the report embedded with the graph by an embedding unit 663 is available in the PC 600 which has made the request. In such a PC 600, the report can be referred in the display 601. This reference may be realized in various manners as described in the second embodiment.

According to the fourth embodiment of the present invention, the person in the service center D can request information regarding expectancy for himself or herself. Therefore, it makes it possible to accommodate various matters in the service center D, if any.

(Fifth Embodiment)

Further, the above mentioned requests may also be made from the CT manufacturer F.

Figure 6:
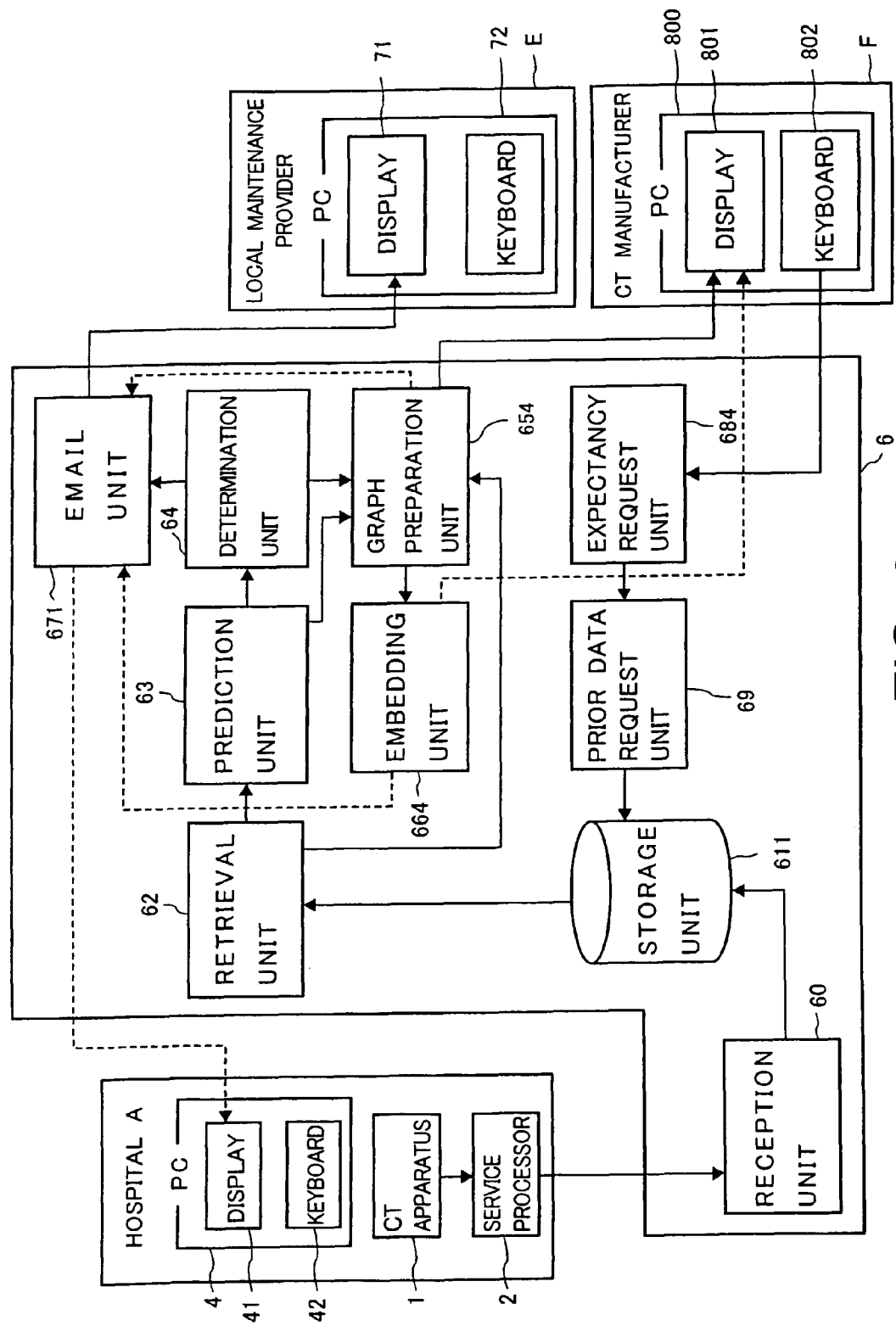
FIG. 6 is a block diagram showing a fifth exemplary configuration of the medical equipment management apparatus in relationship to the hospital and the local maintenance provider according to a fifth embodiment of the present invention.

FIG. 6 is a block diagram showing a fifth exemplary configuration of the medical equipment management apparatus 6 in relationship to the hospital A and the local maintenance provider E according to a fifth embodiment of the present invention.

In FIG. 6, components, which operate in a manner similar to the components shown in FIG. 2 or 3 are given the same reference numbers and detailed explanations are appropriately omitted. In addition, operations of the medical equipment management apparatus 6 are similar to those described in the first or second embodiment except for those described below. Therefore, detailed explanations of such operations similar to those in the first or second embodiment are omitted herein.

When a person in the CT manufacturer F, who has or may not have an access authority to the medical equipment management apparatus 6, operates a keyboard 802 of a PC 800 provided in the CT manufacturer F so as to request an expectancy of parameter data regarding a specific part or the like of the CT apparatus 1, this request is sent to an expectancy request unit 684. The request from the keyboard 802 may be made as in the case of the keyboard 421 described in the second embodiment.

When the request from the PC 800 is received by the expectancy request unit 684 through the network, the expectancy request unit 684 sends a request to the prior data request unit 69 according to a content of the request from the PC 800. The request to the prior data request unit 69 may be as described in the second embodiment. Subsequently, the graph and/or the report are obtained as described in the second embodiment.

When the request from the CT manufacturer F corresponds to a graph, the graph prepared in a graph preparation unit 654 is available in the PC 800 which has made the request. In such a PC 800, the graph can be referred in a display 801. Also when the request from the CT manufacturer F regards a report, the report embedded with the graph by an embedding unit 664 is available in the PC 800 which has made the request. In such a PC 800, the report can be referred in the display 801. This reference may be realized in various manners as described in the second embodiment.

According to the fifth embodiment of the present invention, the person in the CT manufacturer F can request information regarding an expectancy for himself or herself. Therefore, if necessary, he or she can see, for example, whether the CT apparatus 1 manufactured by the CT manufacturer F is operating properly or the CT apparatus 1 is showing any abnormality (any possibility of abnormality). Accordingly, the CT manufacturer F can determine abnormality signs at an early stage, which may not be discovered by other manufacturers who do not manufacture the CT apparatus 1. This improves the credibility of the CT manufacturer F.

(Sixth Embodiment)

In the first to fifth embodiments of the present invention, the requests from PCs have corresponded to a graph or a report. The requests are not limited to those, but also applied to other information, such as, for example, only an expectancy.

Figure 7:
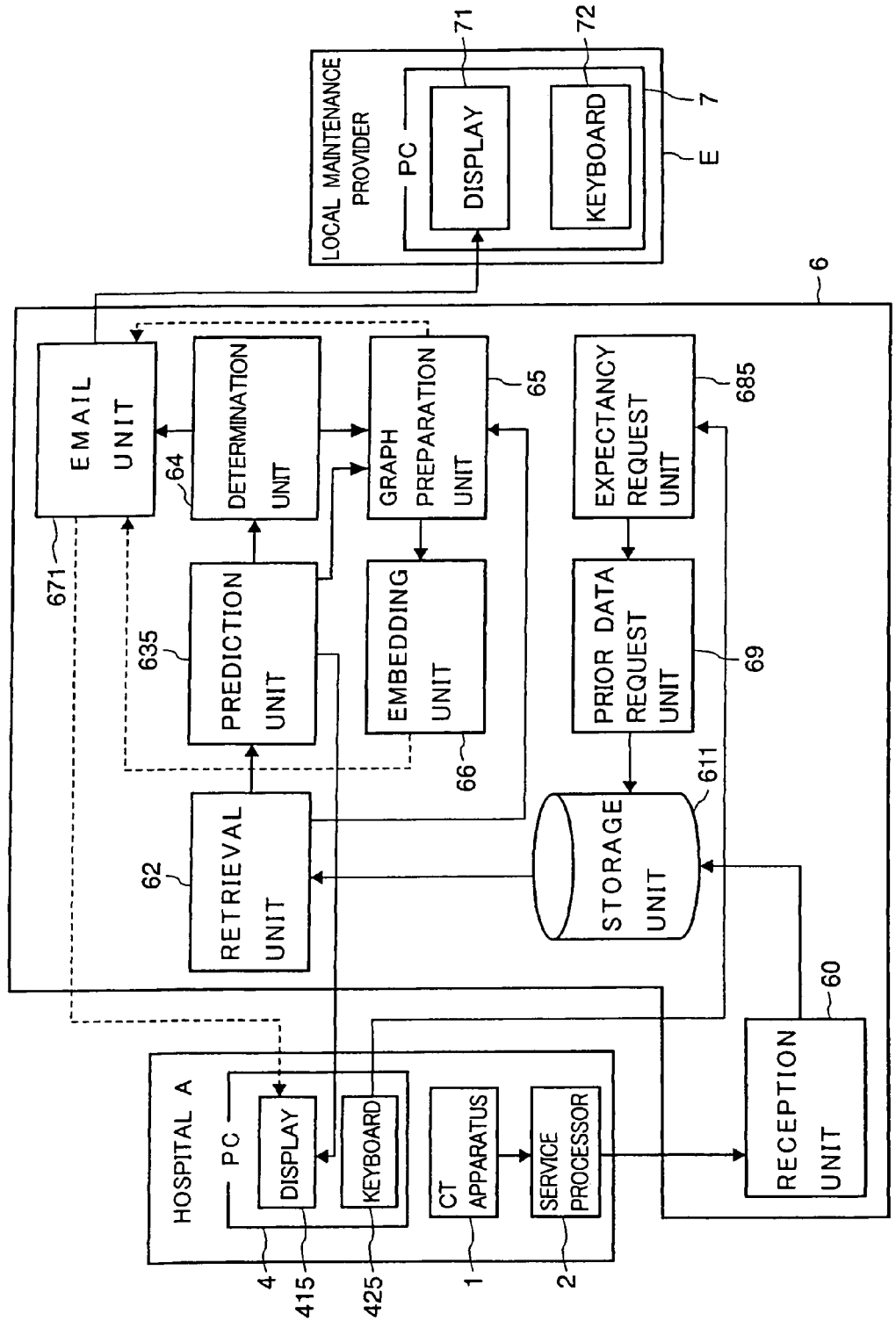
FIG. 7 is a block diagram showing a sixth exemplary configuration of the medical equipment management apparatus in relationship to the hospital and the local maintenance provider according to a sixth embodiment of the present invention.

Turning now to FIG. 7, which is a block diagram showing a sixth exemplary configuration of the medical equipment management apparatus 6 in relationship to the hospital A and the local maintenance provider E according to a sixth embodiment of the present invention.

In FIG. 7, components, which operate in a manner similar to the components shown in FIG. 2 or 3 are given the same reference numbers and detailed explanations are appropriately omitted. In addition, operations of the medical equipment management apparatus 6 are similar to those described in the first or second embodiment except for those described below. Therefore, detailed explanations of such operations similar to those in the first or second embodiment are omitted herein.

When the user in the hospital A operates a keyboard 425 of the PC 4 so as to request an expectancy of parameter data regarding a specific part or the like of the CT apparatus 1, this request is sent to an expectancy request unit 685. The request from the keyboard 425 may be made as in the case of the keyboard 421 described in the second embodiment.

When the request from the PC 4 is received by the expectancy request unit 685 through the network, the expectancy request unit 685 sends a request to the prior data request unit 69 according to a content of the request from the PC 4. The request towards the prior data request unit 69 may be as described in the second embodiment. Subsequently, the expectancy is obtained as described in the second embodiment.

The expectancy predicted in a prediction unit 635 is available in the PC 4 which has made the request. In such a PC 4, the expectancy can be referred in a display 415. This reference may be realized in various manners as described in the second embodiment. A PC which makes the requests is not limited to the PC 4, but may also be other PCs, such as, for example, the PCs 3, 5, 7, 600, and 800.

According to the sixth embodiment of the present invention, it is advantageous for the medical system or, particularly, the PCs, for example, when it is enough to know only an expectancy or when it is preferable to avoid displaying a large size of data for reference.

(Seventh Embodiment)

Instead of the expectancy, the requests may also be applied to a result of the determination based on the expectancy and the predetermined threshold.

Figure 8:
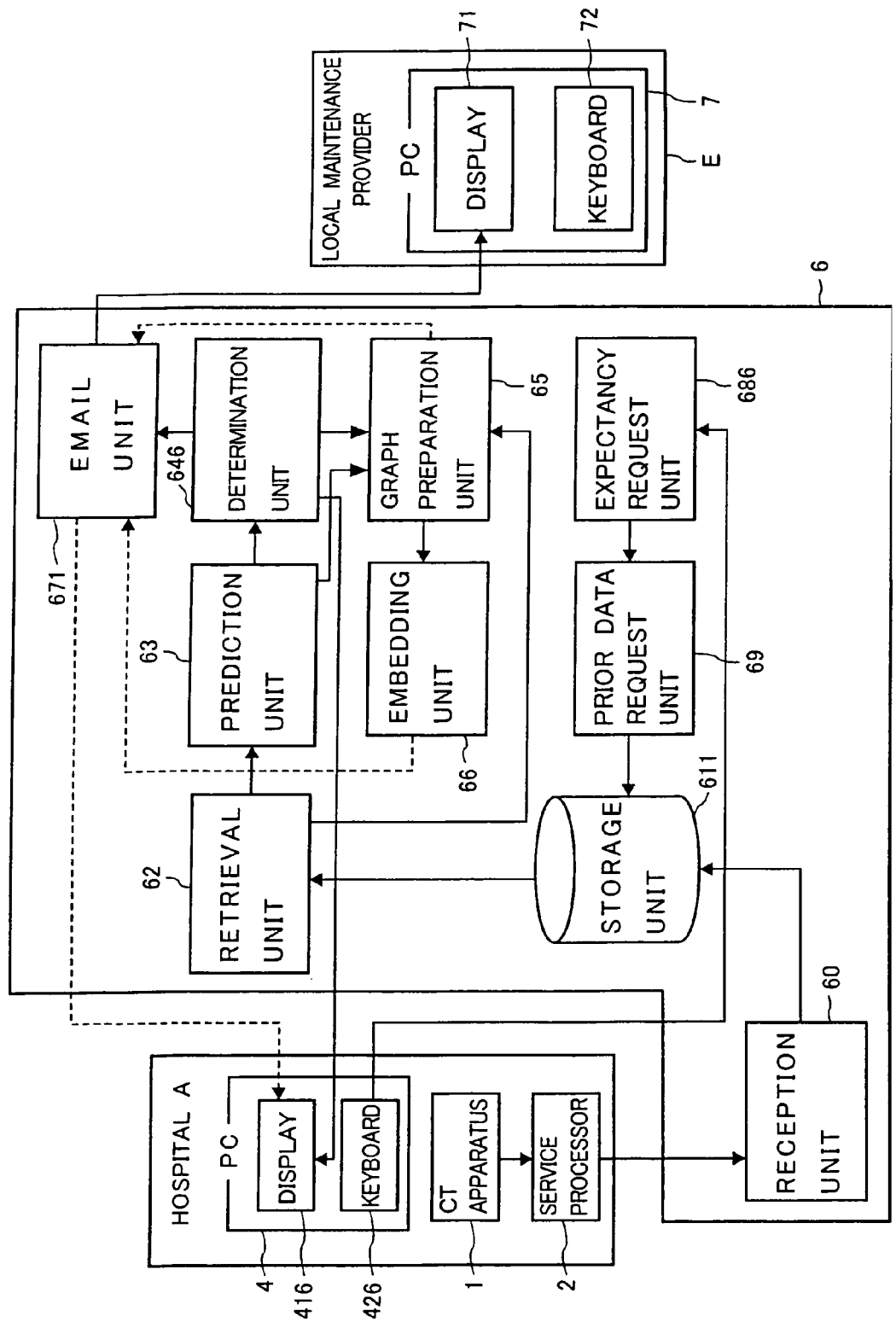
FIG. 8 is a block diagram showing a seventh exemplary configuration of the medical equipment management apparatus in relationship to the hospital and the local maintenance provider according to a seventh embodiment of the present invention.

FIG. 8 is a block diagram showing a seventh exemplary configuration of the medical equipment management apparatus 6 in relationship to the hospital A and the local maintenance provider E according to a seventh embodiment of the present invention.

In FIG. 8, components which operate in a manner similar to the components shown in FIG. 2 or 3 are given the same reference numbers and detailed explanations are appropriately omitted. In addition, operations of the medical equipment management apparatus 6 are similar to those described in the first or second embodiment except for those described below. Therefore, detailed explanations of such operations similar to those in the first or second embodiment are omitted herein.

When the user in the hospital A operates a keyboard 426 of the PC 4 so as to request a result of determination of an expectancy of parameter data regarding a specific part or the like of the CT apparatus 1, this request is sent to an expectancy request unit 686. The request from the keyboard 426 may be made as in the case of the keyboard 421 described in the second embodiment.

When the request from the PC 4 is received by the expectancy request unit 686 through the network, the expectancy request unit 686 sends a request to the prior data request unit 69 according to a content of the request from the PC 4. The request to the prior data request unit 69 may be as described in the second embodiment. Subsequently, a level of the expectancy is determined in a determination unit 646 as described in the second embodiment.

The result of the determination is available in the PC 4 which has made the request. In such a PC 4, the result of the determination can be referred in a display 416. In the reference, for example, a message indicating that the expectancy exceeds the threshold (there is abnormality; an early maintenance is required; there is no problem; and the like) is available when there is only one threshold. When there are two or more thresholds, it is possible to determine which range the expectancy belongs to. In addition or alternatively, a message, such as, for example, that an urgent maintenance is required; a maintenance is required within a predetermined period; a maintenance is not required for the time being; and the like, is available according to which range the expectancy belongs to.

This reference may be realized in various manners as described in the second embodiment. A PC which makes the requests is not limited to the PC 4, but may also be other PCs, such as, for example, the PCs 3, 5, 7, 600, and 800.

According to the seventh embodiment of the present invention, it is advantageous for the medical system or, particularly, the PCs, for example, when it is enough to know only a result of the determination or an emergency level, or when it is preferable to avoid displaying a large size of data for reference.

<Operation Flow>

Operation flows will be described each of which is from a parameter data reception to an expectancy reference. Each of the flows may be applied to, but are not limited to, the medical equipment management apparatus 6 with one or more of the configurations described in the first to seventh embodiments of the present invention. In the embodiments below, however, flowcharts are described based on the medical equipment management apparatus 6 in relationship to the hospital A and the local maintenance provider E shown in FIG. 3, as an example.

(Eighth Embodiment)

Figure 9:
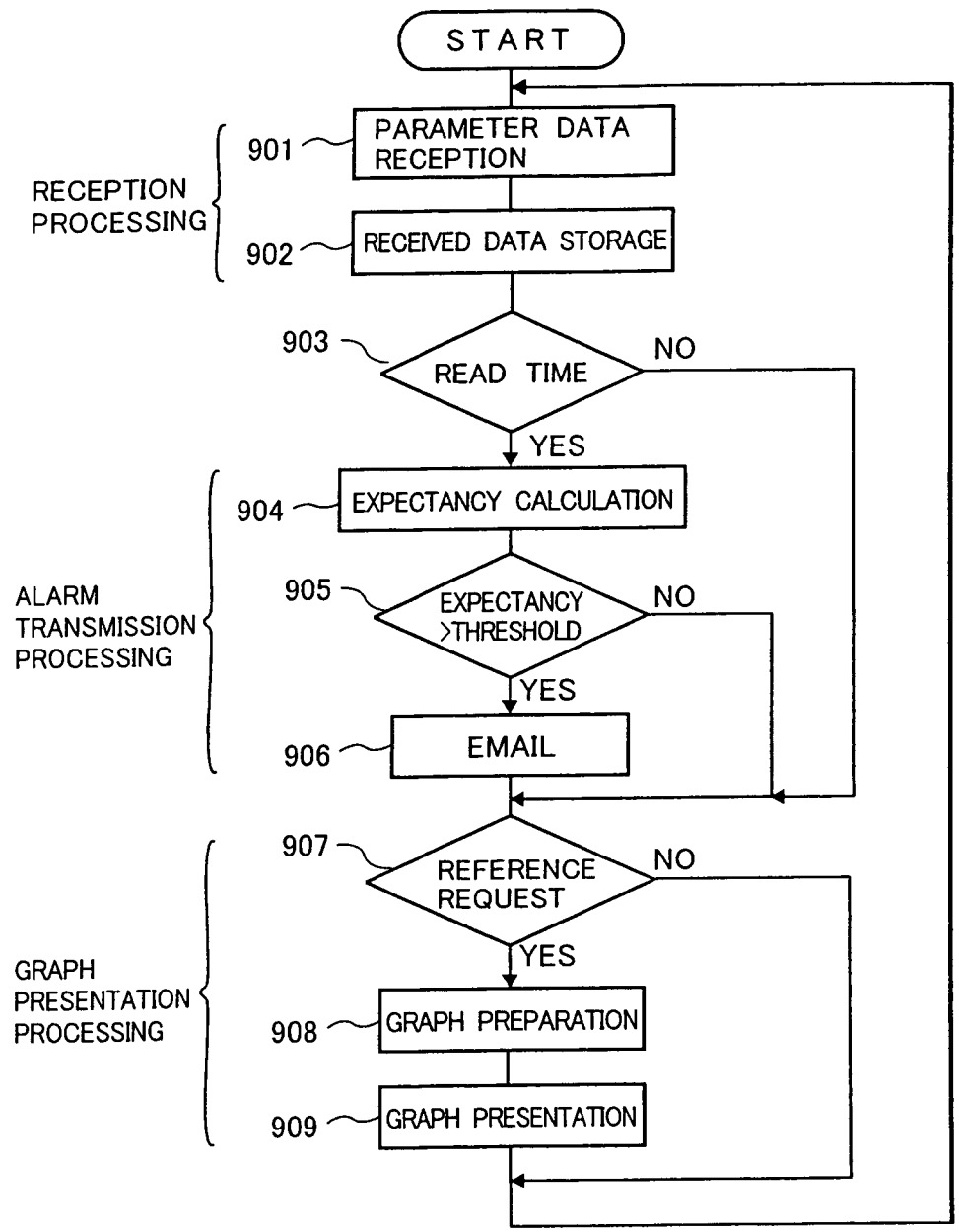
FIG. 9 is a flowchart showing a first exemplary operation of the medical equipment management apparatus according to an eighth embodiment of the present invention.

FIG. 9 is a flowchart showing a first exemplary operation of the medical equipment management apparatus 6 according to an eighth embodiment of the present invention. As shown in FIG. 9, parameter data provided from the service processor 2 connected to the CT apparatus 1 are received by the reception unit 60 (step 901). The received parameter data are stored in the storage unit 611 (step 902).

The stored parameter data are retrieved (or read out) by the retrieval unit 62 every predetermined time. The retrieval may also be implemented for every part included in the CT apparatus 1. In step 903, it is determined whether or not it is time to retrieve the stored parameter data. As long as it is not such a time (step 903 NO) and there is no reference request (step 907 NO), the reception in step 901 and the storage in step 902 are repeated in the event that parameter data are provided from the service processor 2.

In response to the retrieval in the retrieval unit 62, an expectancy of parameter data to be received in the future is predicted by calculation based on the retrieved parameter data in the prediction unit 63 (step 904). The predicted expectancy is compared to a predetermined threshold in the determination unit 64 (step 905). When the expectancy is determined to exceed the predetermined threshold (greater than the upper threshold, if predetermined, or lower than the bottom threshold, if predetermined), an email for informing such a determination is transmitted to the PC 7 provided in the local maintenance provider E (and maybe to the PC 4 provided in the hospital A) by the email unit 671 (step 906). A graph and/or a report may be included in the email as described before.

After the email transmission, it is determined if there is a request corresponding to an expectancy or the like (step 907). The same is also determined in step 907 when the expectancy does not exceed the predetermined threshold in step 905. Further, the same is also determined in step 907 when it is not determined to be a time to retrieve the stored parameter data in step 903.

When it is determined that there is a reference request, the graph preparation unit 651 prepares a graph which compares the parameter data and the expectancy to the predetermined threshold (step 908). The prepared graph may be embedded in a report as described before. The prepared graph is referred to through the WWW browser or the report and displayed in the PC 4 (step 909).

Further, the above described steps are repeated. In addition, the steps 901 to 902 belong to a reception processing, and the steps 903 to 906 belong to an alarm transmission processing. The steps 907 to 909 belong to a graph presentation processing. Any one or more of the above three processes may be implemented simultaneously or in parallel in the medical equipment management apparatus 6.

In step 903, the retrieval time is not limited to every predetermined time period, but can be variously set as described before. For example, the retrieval may be implemented every time parameter data is received from the service processor 2, every time the medical equipment management apparatus 6 is powered on, any time set by the user, any combination of those, or any preferable timing.

Figure 10:
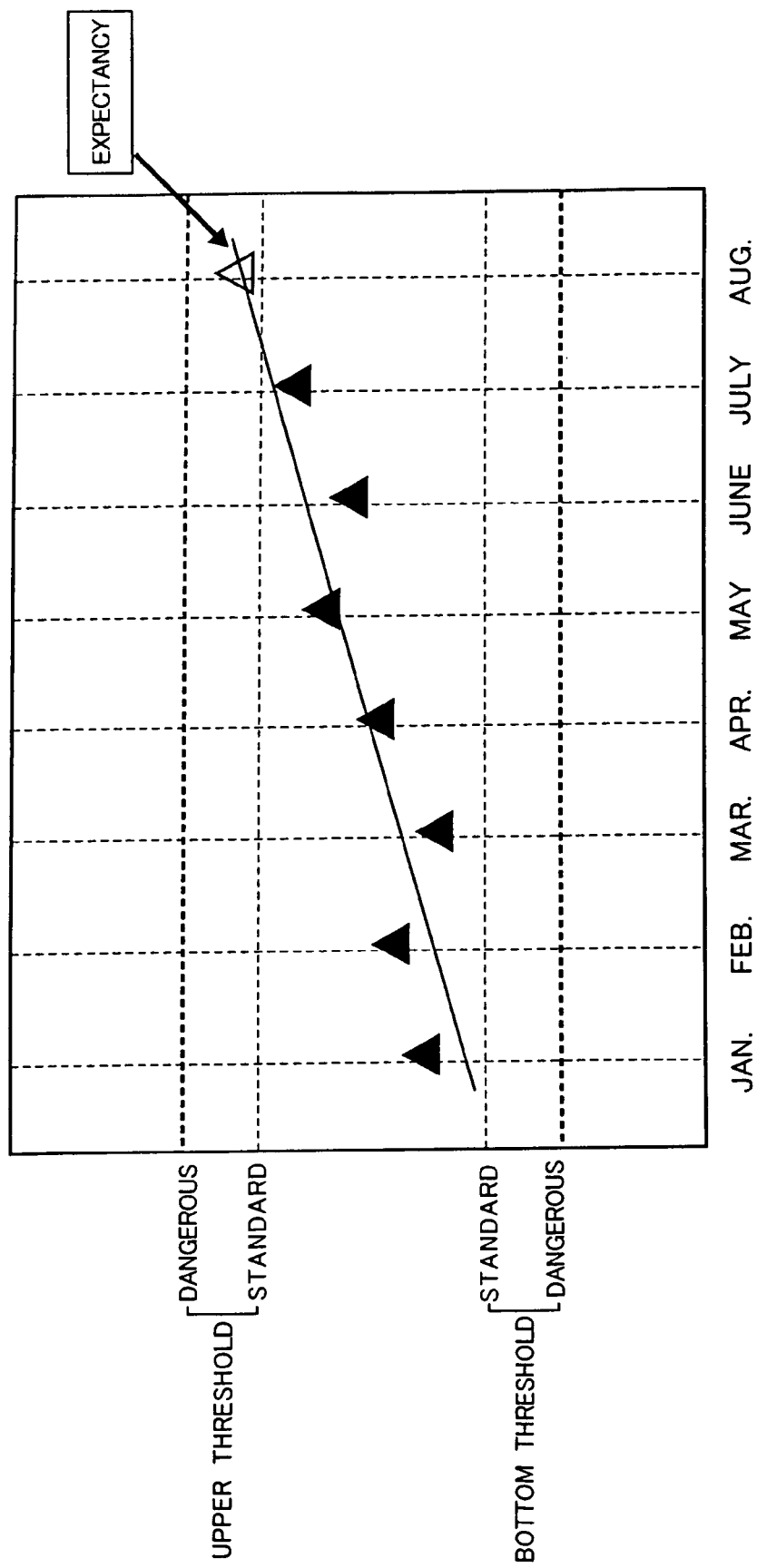
FIG. 10 is an exemplary graph referred to in a PC according to embodiments of the present invention.

Next, FIG. 10 is an exemplary graph referred to in step 909. In FIG. 10, parameter data are plotted in black triangles as prior data from January to July. In addition, an expectancy is plotted in a white triangle as parameter data predicted to be received in August. Further, FIG. 10 includes an upper threshold and a bottom threshold. The upper threshold includes a standard level and a dangerous level. Similarly, the bottom threshold includes a standard level and a dangerous level. Since the expectancy for August exceeds the standard level of the upper threshold, an email is transmitted by the email unit 671. Still further, the graph shows a linear function which was obtained based on the parameter data and has become a base of the prediction.

(Ninth Embodiment)

In the eighth embodiment, the expectancy was predicted every predetermined period or so described before regardless of reference requests from the PC 4. However, the expectancy may be predicted in response to reference requests from the PC 4.

Figure 11:
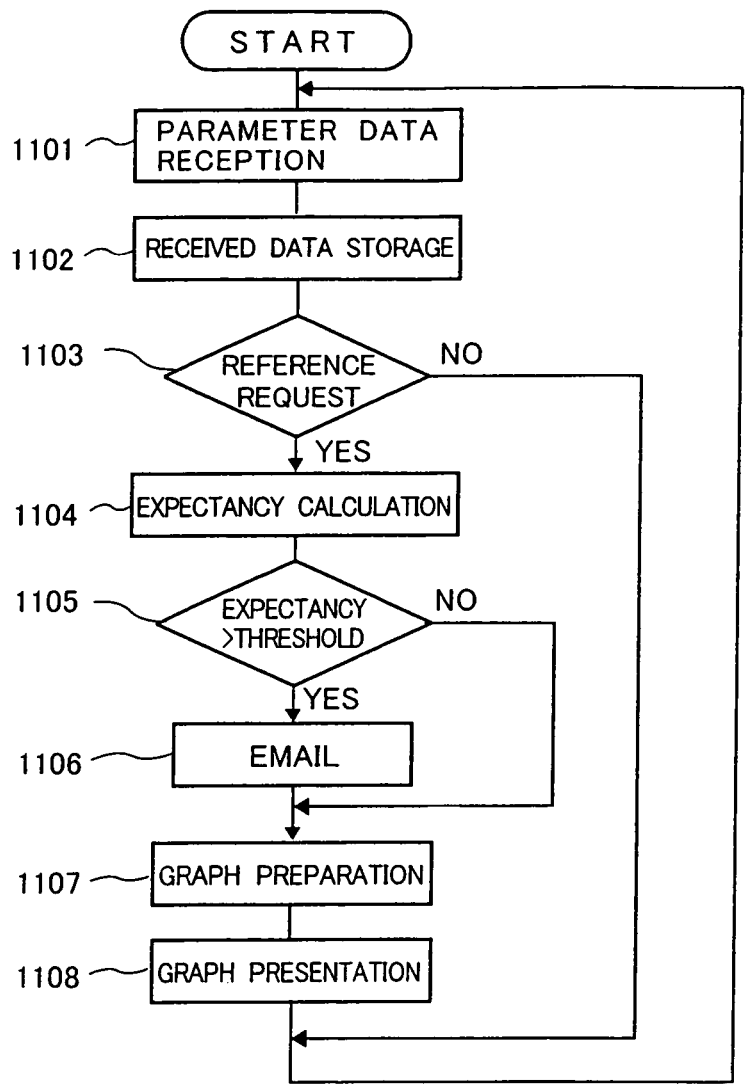
FIG. 11 is a flowchart showing a second exemplary operation of the medical equipment management apparatus according to a ninth embodiment of the present invention.

Next, FIG. 11 is a flowchart showing a second exemplary operation of the medical equipment management apparatus 6 according to a ninth embodiment of the present invention. As shown in FIG. 11, parameter data provided from the service processor 2 connected to the CT apparatus 1 are received by the reception unit 60 (step 1101). The received parameter data are stored in the storage unit 611 (step 1102).

It is determined if there is a request for referring to an expectancy or the like (step 1103). When there is no reference request (step 1103 NO), the reception in step 1101 and the storage in step 1102 are repeated in the event that parameter data are provided from the service processor 2.

When it is determined that there is the reference request, the stored parameter data regarding a part of the CT apparatus 1 are retrieved (or read out) by the retrieval unit 62 according to the reference request. In response to the retrieval in the retrieval unit 62, an expectancy of parameter data to be received in the future is predicted by calculation based on the retrieved parameter data in the prediction unit 63 (step 1104). The predicted expectancy is compared to a predetermined threshold in the determination unit 64 (step 1105). When the expectancy is determined to exceed the predetermined threshold (greater than the upper threshold, if predetermined, or lower than the bottom threshold, if predetermined), an email for informing such a determination is transmitted to the PC 7 provided in the local maintenance provider E (and maybe to the PC 4 provided in the hospital A) by the email unit 671 (step 1106). A graph and/or a report may be included in the email as described before.

After the email transmission, the graph preparation unit 651 prepares a graph which compares the parameter data and the expectancy to the predetermined threshold (step 1107). The prepared graph may be embedded in a report as described before. The graph is also prepared when the expectancy does not exceed the predetermined threshold in step 1105. The prepared graph is referred to through the WWW browser or the report and displayed in the PC 4 (step 1108).

The above described steps are repeated.

In the eighth and ninth embodiments, even if it is not a case by the email transmission or the reference request, the expectancy and/or the graph may be referred to by a person who receives the report regularly, in the event of an emergency, and/or in response to requests, as long as the report is embedded with expectancy or the graph.

(First Modification)

When there are dual threshold levels as shown in FIG. 10, such as the standard level and the dangerous level, flowcharts shown in FIGS. 9 and 11 may be modified to transmit emails to different addresses according to a relationship between expectancy and threshold levels, respectively.

Figure 12A:
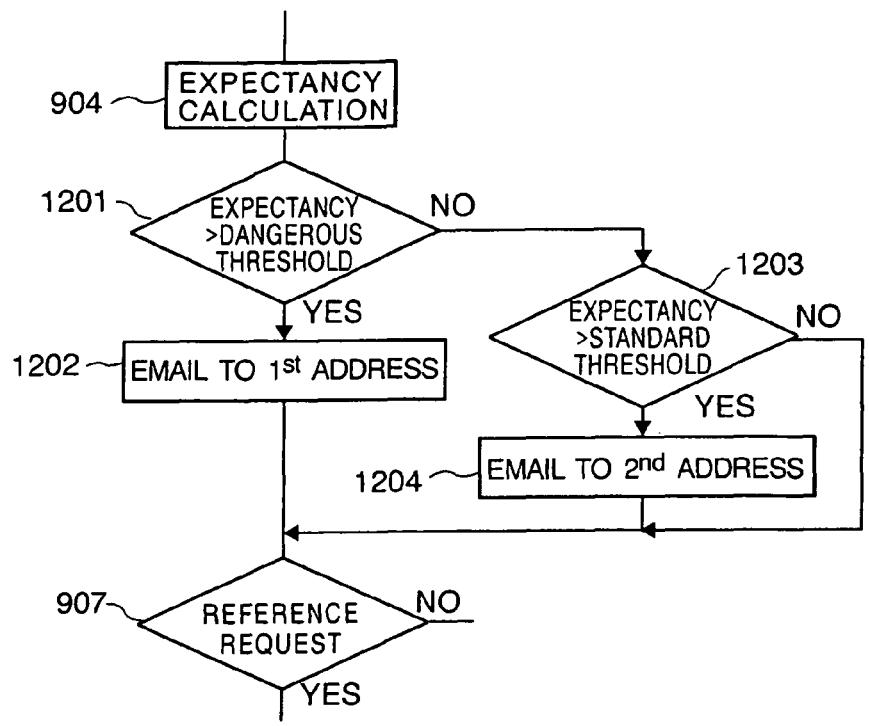
FIG. 12A is a flowchart showing a first example modifying a part of the flowchart shown in FIG. 9.
Figure 12B:
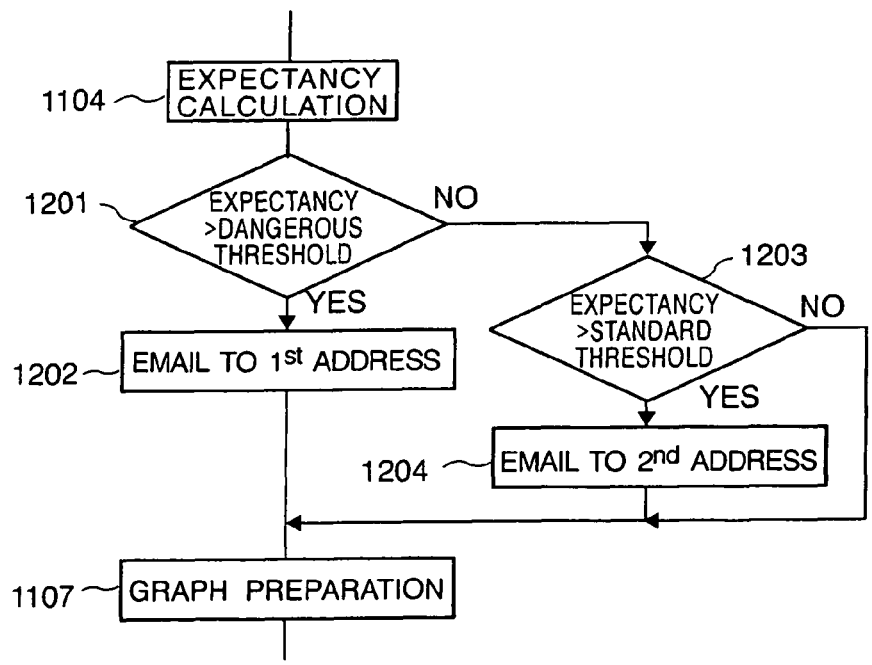
FIG. 12B is a flowchart showing a first example modifying a part of the flowchart shown in FIG. 11.

FIG. 12A is a flowchart showing a first example modifying a part of the flowchart shown in FIG. 9. Similarly, FIG. 12B is a flowchart showing a first example modifying a part of the flowchart shown in FIG. 11. In both FIGS. 12A and 12B, an expectancy is first compared to the dangerous level when the expectancy is compared to the predetermined threshold (step 1201).

When the expectancy is determined to exceed the dangerous level (greater than the dangerous level of the upper threshold, if predetermined, or lower than the dangerous level of the bottom threshold, if predetermined), an email for informing such a determination is transmitted to a first group of addresses (or a first address) by the email unit 671 (step 1202). The first group of addresses may include the PC 7 provided in the local maintenance provider E and the PC 4 in the hospital A.

When the expectancy is not determined to exceed the dangerous level in step 1201, the expectancy is then compared to the standard level (step 1203). When the expectancy is determined to exceed the standard level (greater than the standard level of the upper threshold, if predetermined, or lower than the standard level of the bottom threshold, if predetermined), an email for informing such a determination is transmitted to a second group of addresses (or a second address) by the email unit 671 (step 1204). The second group of addresses may include only the PC 7. Alternatively, the second group of addresses may be the same as the first group of addresses.

Instead of the comparisons described above, the expectancy may first be compared to the standard level. Further, instead of transmitting emails to different group of addresses, contents of emails may be differentiated according to the comparisons. For example, when the expectancy is determined to exceed the dangerous level in step 1201, an email including a first message is transmitted to both the PC 7 and the PC 4 by the email unit 671. The first message is, for example, for asking the maintenance personnel to go to the hospital A to implement inspection and a maintenance service. Similarly, when the expectancy is determined to exceed the standard level in step 1203, an email including a second message is transmitted to both the PC 7 and the PC 4 by the email unit 671. The second message is, for example, for suggesting it is not necessary for immediate maintenance if a next regular maintenance service is scheduled within a month, but, otherwise, asking the maintenance personnel to implement inspection and a maintenance service within two months.

(Second Modification)

The flowcharts shown in FIGS. 9 and 11 may be modified to prepare and provide a graph showing a probable date according to the reference request from the PC 4.

Figure 13A:
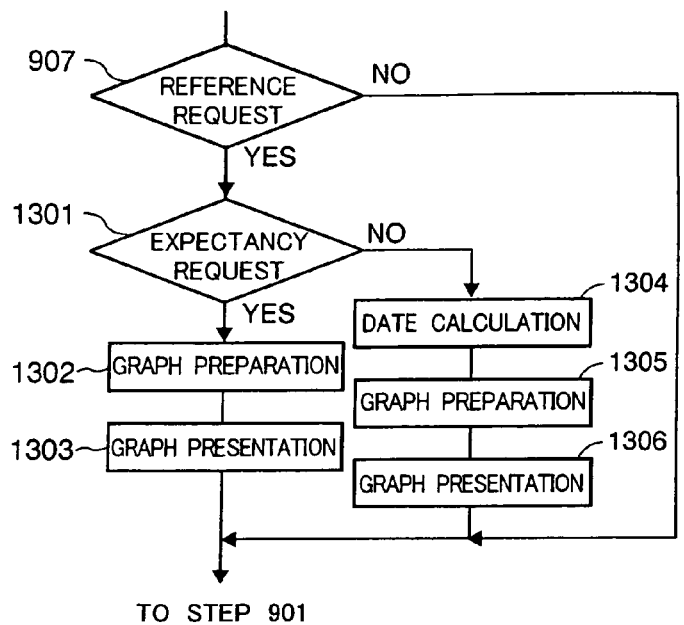
FIG. 13A is a flowchart showing a second example modifying a part of the flowchart shown in FIG. 9.
Figure 13B:
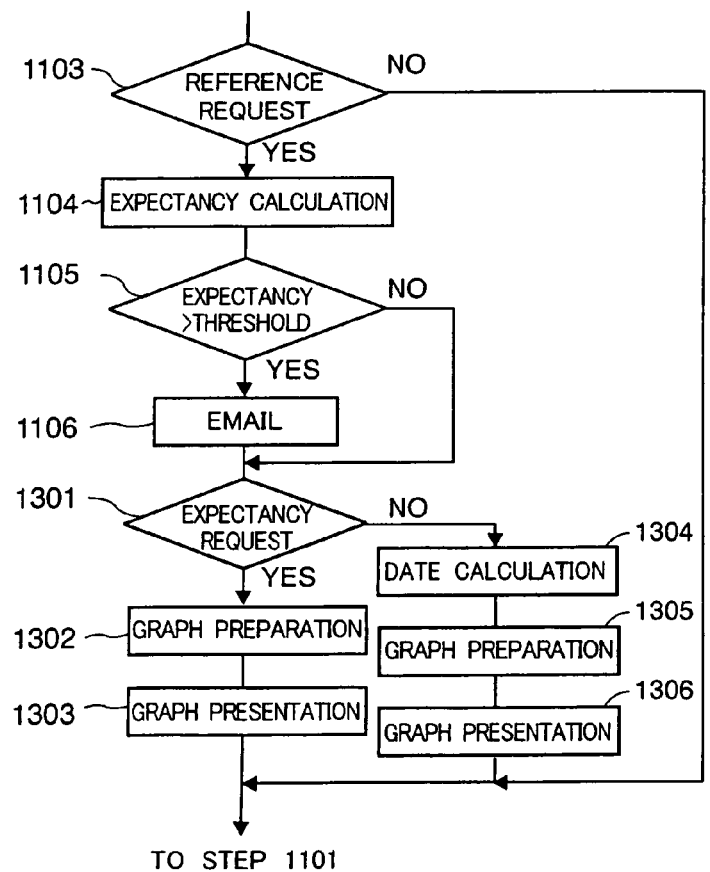
FIG. 13B is a flowchart showing a second example modifying a part of the flowchart shown in FIG. 11.

FIG. 13A is a flowchart showing a second example modifying a part of the flowchart shown in FIG. 9. Similarly, FIG. 13B is a flowchart showing a second example modifying a part of the flowchart shown in FIG. 11. In both FIGS. 13A and 13B, when there was the reference request, it is determined whether the reference request corresponds an expectancy or probable date (step 1301).

When the reference request is determined to correspond to the expectancy, the graph preparation unit 651 prepares a graph showing the expectancy based on the reference request (e.g., a requested part of the CT apparatus 1) (step 1302). The prepared graph may be, for example, as shown in FIG. 10. Further, the prepared graph may be embedded in a report as described before. The prepared graph is provided (presented) for reference through the WWW browser or the report and displayed in the PC 4 (step 1303).

Figure 14:
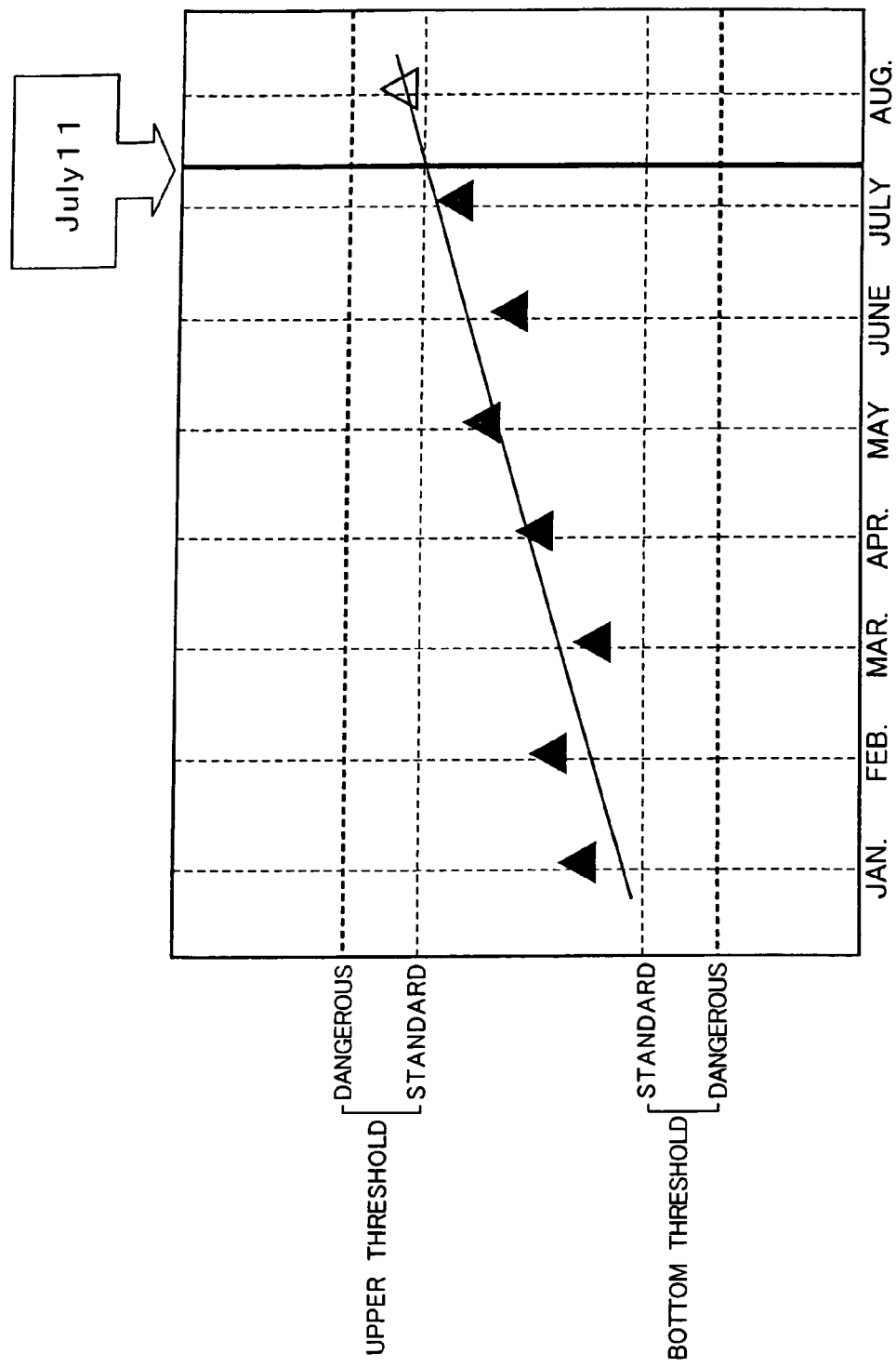
FIG. 14 is another exemplary graph referred to in a PC according to embodiments of the present invention.

On the other hand, when the reference request is determined to correspond to the probable date, the probable date is determined by calculation based on the parameter data and the expectancy in the determination unit 64 (step 1304). The graph preparation unit 651 prepares a graph showing the probable date based on the reference request (step 1305). The prepared graph may be, for example, as shown in FIG. 14. In FIG. 14, the probable date is July 11. The prepared graph may be embedded in a report as described before, and the prepared graph is provided (presented) for reference through the WWW browser or the report and displayed in the PC 4 (step 1306).

When there are two or more threshold levels of the predetermined threshold, the user may designate which level the probable date should correspond to in the reference request. Alternatively, probable dates corresponding to respective threshold levels may be shown in a graph whether a specific threshold level is indicated in the reference request or not.

(Third Modification)

As described in the second modification, when both the expectancy request and the probable date request are acceptable, minimum information, such as an expectancy and a probable date, may be provided (presented) for reference, instead of the graph.

Figure 15A:
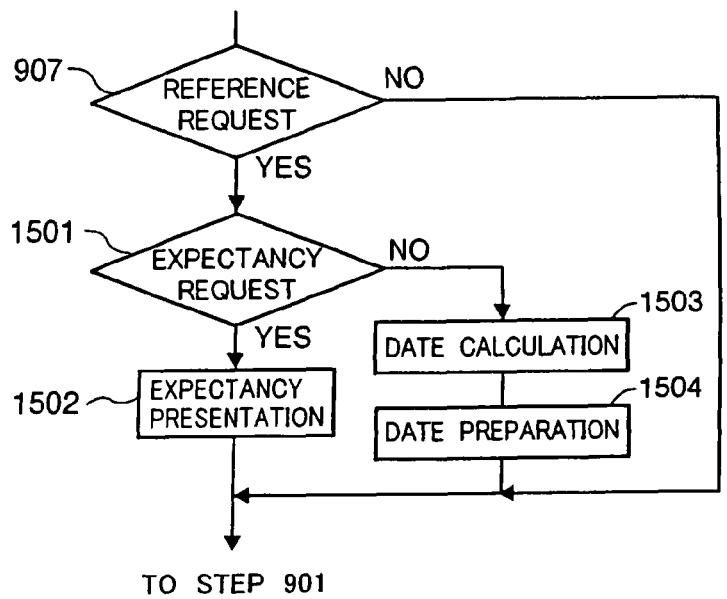
FIG. 15A is a flowchart showing a third example modifying a part of the flowchart shown in FIG. 9.
Figure 15B:
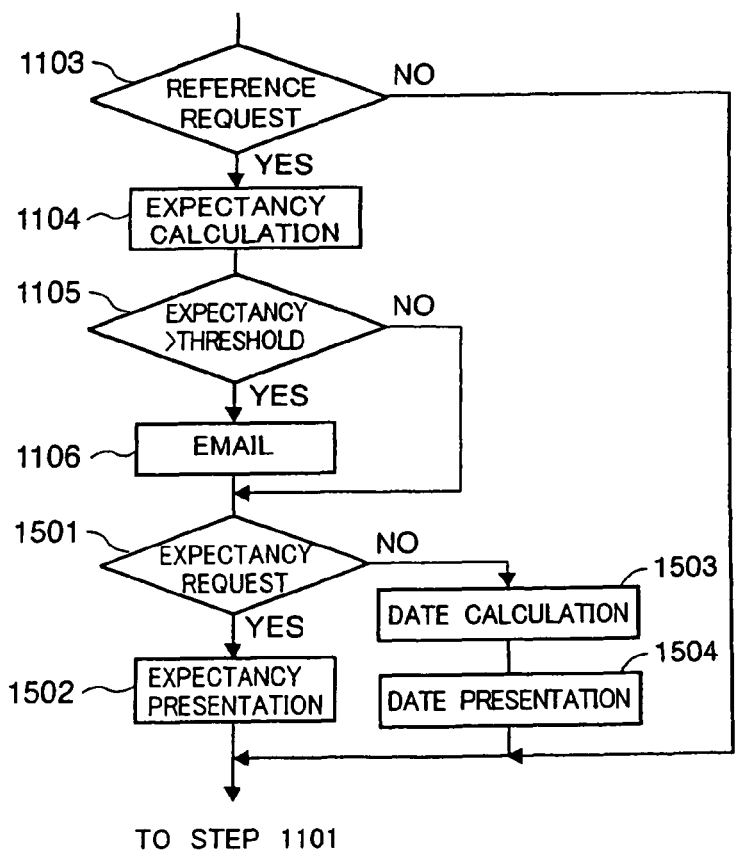
FIG. 15B is a flowchart showing a third example modifying a part of the flowchart shown in FIG. 11.

Next, FIG. 15A is a flowchart showing a third example modifying a part of the flowchart shown in FIG. 9. Similarly, FIG. 15B is a flowchart showing a third example modifying a part of the flowchart shown in FIG. 11. In both FIGS. 15A and 15B, when there was the reference request, it is determined whether the reference request corresponds to an expectancy or probable date (step 1501).

When the reference request is determined to correspond to the expectancy, the expectancy based on the reference request (e.g., a requested part of the CT apparatus 1) is provided (presented) for reference through the WWW browser or a report, if embedded, and displayed in the PC 4 (step 1502).

On the other hand, when the reference request is determined to correspond to the probable date, the probable date is determined by calculation based on the parameter data and the expectancy in the determination unit 64 (step 1503). The probable date based on the reference request (e.g., a requested part of the CT apparatus 1) is provided (presented) for reference through the WWW browser or a report, if embedded, and displayed in the PC 4 (step 1504).

When there are two or more threshold levels of the predetermined threshold, the user may designate which level the probable date should correspond to in the reference request. Alternatively, probable dates corresponding to respective threshold levels may be provided whether or not a specific threshold level is indicated in the reference request.

(Tenth Embodiment)

As described in the embodiments of the present invention, an email is transmitted to the local maintenance provider E when an expectancy exceeds the predetermined threshold. Such an email transmission may be controlled in accordance with a contract made between the hospital A and the CT manufacturer F or the local maintenance provider E.

Figures 16, 17:
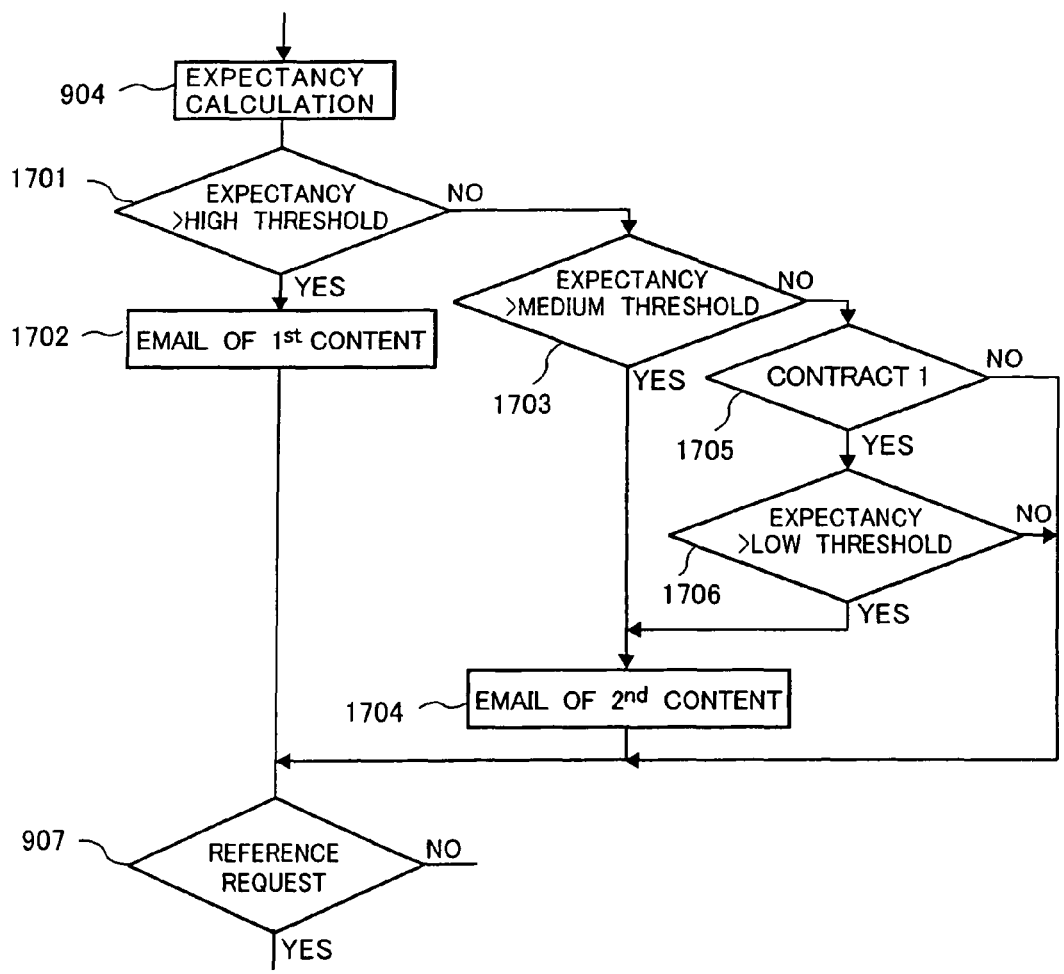
FIG. 16 is a table showing an exemplary relationship between types of contracts and email transmission including what is instructed in the email according to a tenth embodiment of the present invention.
FIG. 17 is a flowchart showing a fourth example modifying a part of the flowchart shown in FIG. 9 according to a tenth embodiment of the present invention.

Turning now to FIG. 16, which is a table showing an exemplary relationship between types of contracts and email transmission rules including what is instructed in the email according to a tenth embodiment of the present invention.

In FIG. 16, the maintenance necessity is categorized into four levels including three abnormality levels and a normal level regarding operations of the CT apparatus 1. The three abnormality levels are 'high', 'medium', and 'low'. Contract 1 aims at reducing as many risks as possible which causes affections against operations of the CT apparatus 1, such as, for example, CT examinations. An amount of the contract 1 is high. Even when the abnormality level is low, an email is transmitted to the local maintenance provider E so as to give a notice of the current situation. In contrast, contract 2 has some risk. When the abnormality level is low, no email is transmitted to the local maintenance provider E. An amount of the contract 2 is, however, reasonable.

Under the condition in the table shown in FIG. 16, operations of the medical equipment management apparatus 6 will be described with reference to FIG. 17. FIG. 17 is a flowchart showing a fourth example modifying a part of the flowchart shown in FIG. 9 according to a tenth embodiment of the present invention. There is no figure showing an example modifying a part of the flowchart shown in FIG. 11 according to the tenth embodiment of the present invention. However, a flowchart similar to that shown in FIG. 17 is also applied as a modification of a part of the flowchart shown in FIG. 11.

In the tenth embodiment, the table shown in FIG. 17 is stored, for example, in the determination unit 64. After an expectancy is predicted, the expectancy is first compared to a high threshold level corresponding to the abnormality level 'high' (step 1701).

When the expectancy is determined to exceed the high threshold level, an email having a first content is transmitted to at least the PC 7 provided in the local maintenance provider E by the email unit 671 (step 1702). The first content may be a message instructing an urgent replacement of a part of the CT apparatus 1 regarding the expectancy. This email is transmitted whether it is the contract 1 or 2.

When the expectancy is determined not to exceed the high threshold level in step 1701, the expectancy is then compared to a medium threshold level corresponding to the abnormality level 'medium' (step 1703). When the expectancy is determined to exceed the medium threshold level, an email having a second content is transmitted to at least the PC 7 by the email unit 671 (step 1704). The second content may be a message instructing a replacement of a part of the CT apparatus 1 regarding the expectancy in the next regular maintenance service. This email is transmitted whether it is the contract 1 or 2.

When the expectancy is determined not to exceed the medium threshold level in step 1703, a type of contract is determined (step 1705). When the type of contract is determined to be the contract 1, the expectancy is further compared to a low threshold level corresponding to the abnormality level 'low' (step 1706). When the expectancy is determined to exceed the low threshold level, an email having the second content is transmitted to at least the PC 7 by the email unit 671 (step 1704). When the type of contract is determined not to be the contract 1 (i.e., determined to be a contract B) in step 1705, no email is transmitted.

A CC (carbon copy) of the email to the PC 7 may be transmitted to the PC 4 and/or others. This lets the user and/or other hospital staff know that the same email is transmitted to the local maintenance provider E. Further, the user and/or other hospital staff can see the current situation of the CT apparatus 1 and take necessary actions and preparations for the situation. Instead of the CC, an email with an original message may be transmitted to the PC 4 and/or others.

(Fourth Modification)

Figure 18:
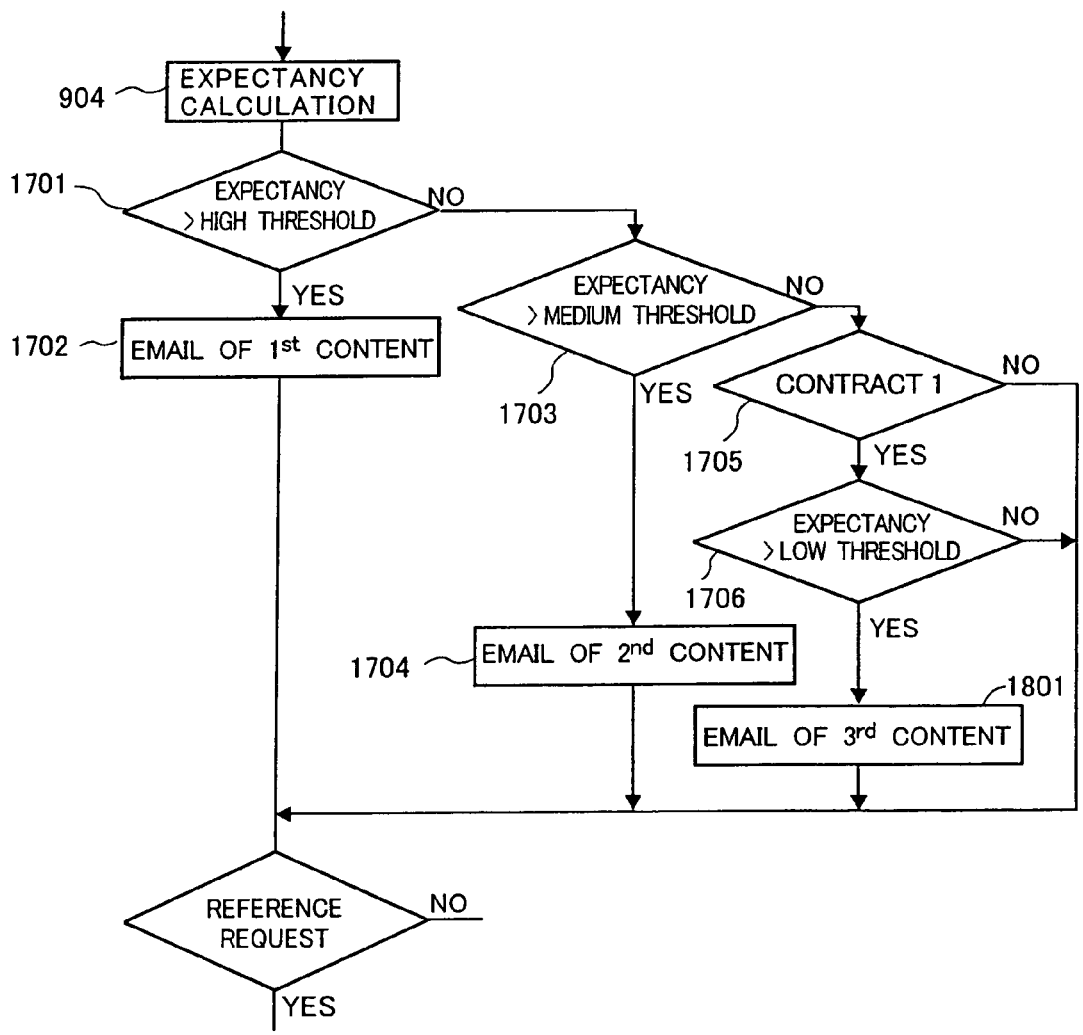
FIG. 18 is a flowchart showing a first example modifying a part of the flowchart shown in FIG. 18.

FIG. 18 is a flowchart showing a first example modifying a part of the flowchart shown in FIG. 18. In the flowchart shown in FIG. 17, the email having the second content is transmitted when the expectancy is determined to exceed the low threshold level in step 1706. As shown in FIG. 18, however, with such a determination, an email having a third content may be transmitted by the email unit 671, instead of the email having the second content (step 1801). The third content is different from the first and second contents. A flowchart similar to that shown in FIG. 18 is also applied as a modification of a part of the flowchart shown in FIG. 11.

Despite the flowcharts in FIG. 17 or 18, a type of contract may be determined first. After the determination, an expectancy predicted may be compared to predetermined threshold levels in accordance with a flowchart regarding the determined contract.

According to the tenth embodiment and the fourth modification, the hospital A can choose a contract type according to a cost effectiveness and operations although there may be some risk as described above in a lower amount of contract. The contract type may be changeable by the hospital A, for example, through the WWW browser over the Internet web site.

(Eleventh Embodiment)

Figure 19:
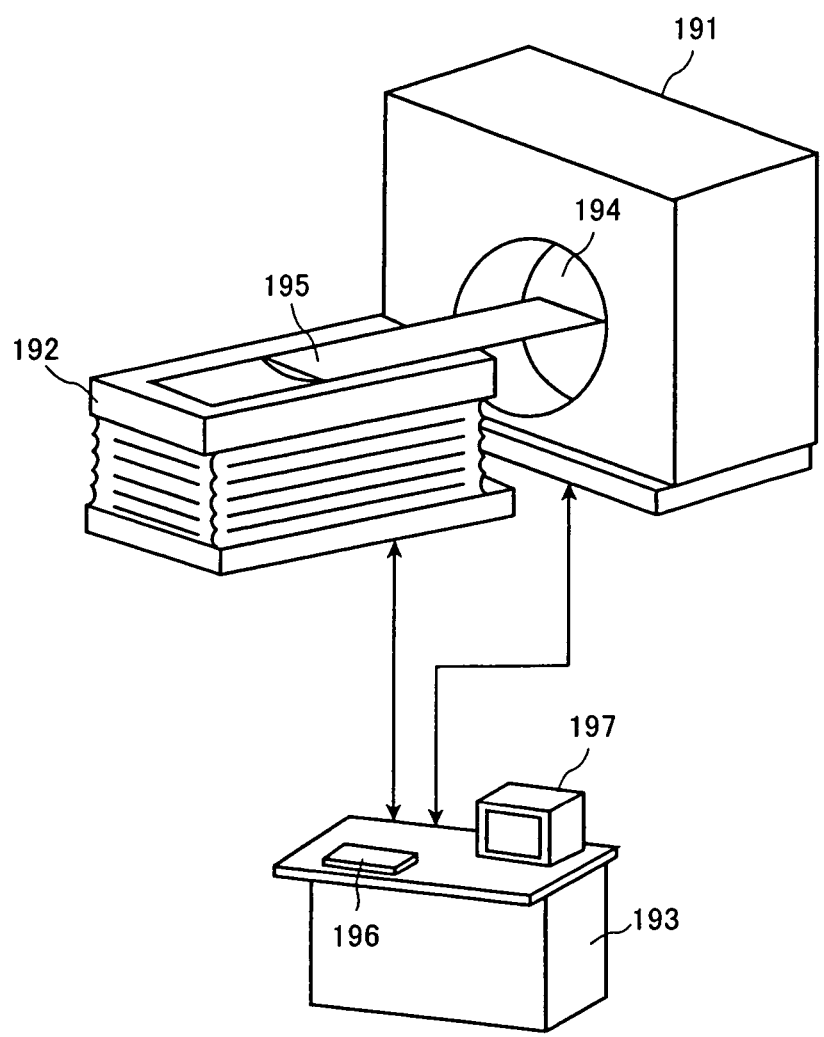
FIG. 19 is an illustration showing an exemplary overview of a CT apparatus according to an eleventh embodiment of the present invention.

The CT apparatus 1 will now be described with reference to FIGS. 19 to 22. The CT apparatus 1 according to an eleventh embodiment of the present invention has an urgent response feature of managing the CT apparatus 1 to operate properly for the time being in case of abnormality occurrence. FIG. 19 is an illustration showing an exemplary overview of the CT apparatus 1 according to the eleventh embodiment of the present invention.

As shown in FIG. 19, the CT apparatus 1 includes a gantry 191, a specimen couch 192, and a console unit 193. The gantry 191 has an opening 194 where radiography is implemented. The specimen couch 192 is placed in front of the gantry 191, and has a table 195 where a specimen lies. The gantry 191 and the specimen couch 192 are controlled from the console unit 193. Further, a height of the specimen couch 192 is adjusted, if necessary, by operations in the console unit 193. The table 195 is slid towards and away from the gantry 191 by operations in the console unit 193. Therefore, the specimen lying on the table 195 is inserted into the opening 194 in the radiography. The console unit 193 controls components of the CT apparatus 1 systematically. Further, the console unit 193 has an input device 196 and a monitor 197. The input device 196 is, for example, equipped with a keyboard and/or a pointing device, such as a mouse, a trackball, a joystick, and/or the like. The console unit 193 accommodates a control unit which will be described later.

Figure 20:
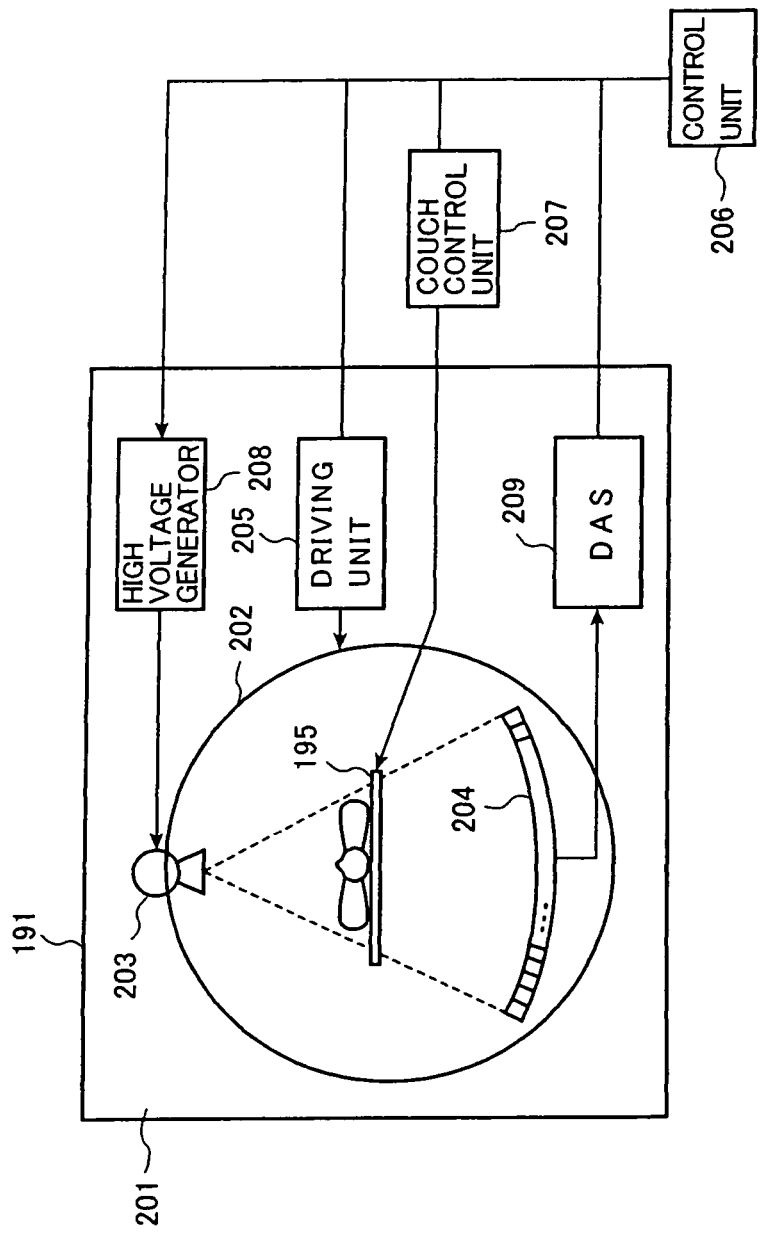
FIG. 20 is a schematic diagram showing further exemplary details of the CT apparatus according to the eleventh embodiment of the present invention.

Next, FIG. 20 is a schematic diagram showing further exemplary details of the CT apparatus 1 according to the eleventh embodiment of the present invention.

As shown, the gantry 191 includes a fixed part 201 and a rotation part 202. The rotation part 202 is supported by the fixed part 201 and is allowed to rotate around the specimen inserted in the opening 194. The rotation part 202 is provided with an X-ray tube 203 and an X-ray detector 204 opposing the X-ray tube 203. Therefore, the specimen lying on the table 195 is placed between the X-ray tube 203 and the X-ray detector 204 in the opening 194. An X-ray radiated from the X-ray tube 203 is an X-ray beam in a conical form. The radiated X-ray is collimated by a slit (or a collimator) provided nearby the X-ray tube 203 so as to be formed in a desired size. The collimated sectorial X-ray is exposed to the specimen. Also, the X-ray transmitted through the specimen (an X-ray resulting from the X-ray radiation) is detected by the X-ray detector 204. The X-ray detector 204 has a plurality of detecting elements aligned in a one-dimensional form. Further, the X-ray detector 204 may alternatively have a plurality of detecting elements arrayed in a two-dimensional form.

The X-ray tube 203 and the X-ray detector 204 are fixed on the rotation part 202 and so continuously rotated around the specimen. The rotation part 202 is driven by a rotation driving unit 205 based on control signals supplied from a control unit 206. In addition, the specimen couch 192 also includes a couch control unit 207 controlling, for example, the table 195 based on couch control signals supplied from the control unit 206. The couch control unit 207 controls the table 195 to move to a predetermined slice position by a predetermined distance intermittently or to move over a predetermined scan range continuously.

The X-ray tube 203 is connected to a high voltage generator 208. The high voltage generator 208 determines an X-ray tube current, an X-ray tube voltage, and the like to be supplied to the X-ray tube 203 on the basis of X-ray control signals supplied from the control unit 206. Accordingly, the X-ray tube 203 radiates the X-ray at predetermined timings.

The X-ray detector 204 is connected to a data acquisition system (hereinafter referred to as a DAS) 209. Further, the DAS 209 acquires projection data reflecting an X-ray transmission factor of each X-ray pulse obtained from the X-ray detector 204 on the basis of data acquisition control signals supplied from the control unit 206. The DAS 209 includes an integrator and an analog to digital converter (hereinafter referred to as an A/D converter) although the integrator and the A/D converter are not shown in FIG. 20. The integrator temporally integrates signals output from each detecting element of the X-ray detector 204, and the A/D converter converts signals output from the integrator into digital signals.

In the CT apparatus 1 configured as described above, data transmitted between the fixed part 201 and the rotation part 202 are amplified by amplifying units provided in a data transmission system. The data transmission system includes transmission systems and reception systems. Further, one of the reception systems is provided in the fixed part 201. The reception system includes an amplifying unit for amplifying detection data signals transmitted from a transmission system provided in the rotation part 202. Another reception system is provided in the rotation part 202 and includes another amplifying unit for amplifying control signals for controlling, for example, the X-ray tube 203 and the rotation part 202, which are transmitted from a transmission system provided in the fixed part 201. In addition, the transmission between the fixed part 201 and the rotation part 202 is, for example, made in an optical signal form according to the eleventh embodiment of the present invention.

Figure 21:
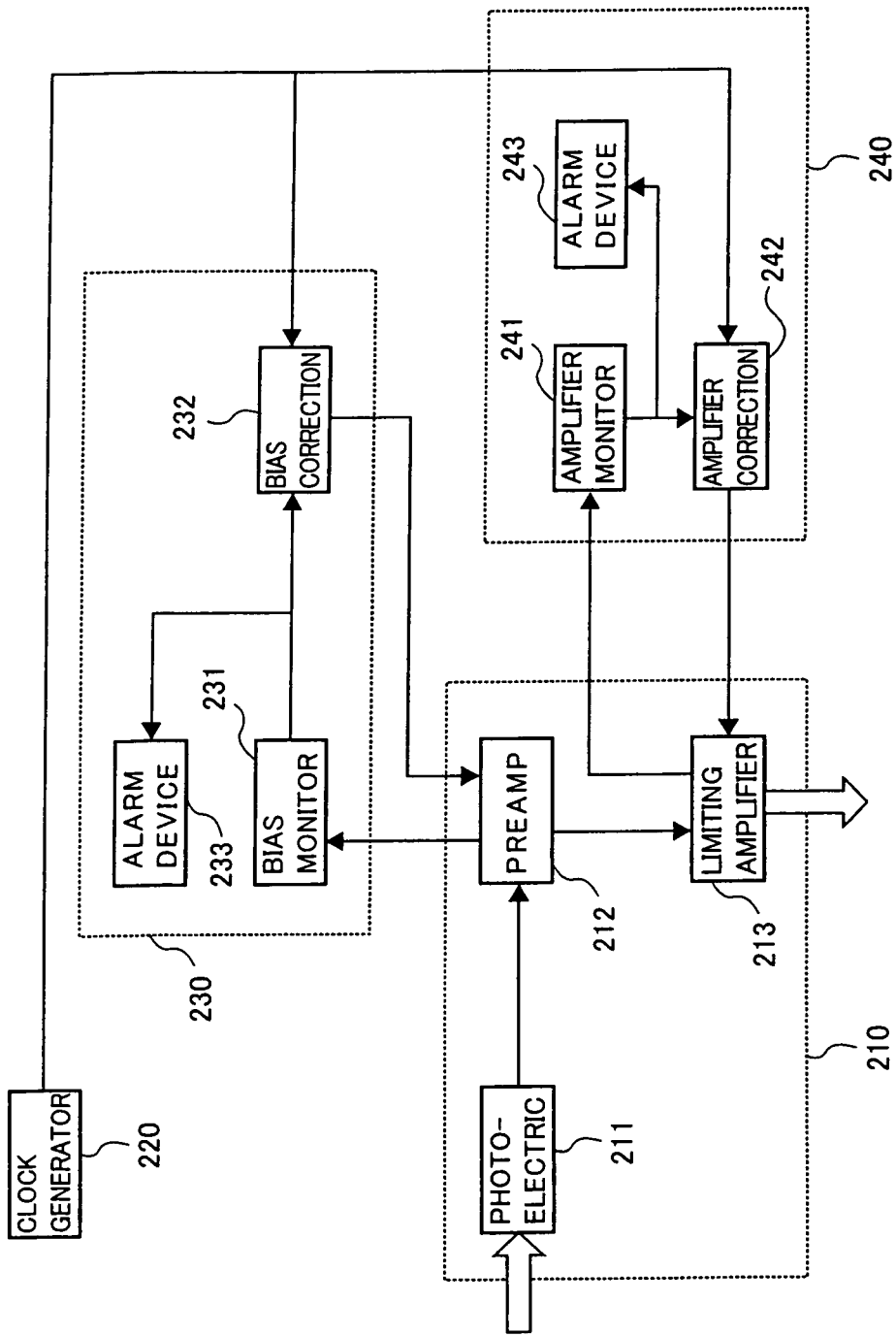
FIG. 21 is a block diagram showing an exemplary configuration of an amplifying unit according to the eleventh embodiment of the present invention.

FIG. 21 is a block diagram showing an exemplary configuration of the amplifying unit provided in the fixed part 201 or the rotation part 202 according to the eleventh embodiment of the present invention. As shown, the amplifying unit includes a photo receiving unit 210, a clock generator 220, a bias voltage control unit 230, and an amplitude voltage control unit 240.

The photo receiving unit 210 includes a photoelectric conversion device 211, a preamplifier 212, and a limiting amplifier 213. The photoelectric conversion device 211 includes a photodiode, for example. The photoelectric conversion device 211 receives optical signals transmitted from an electric-photo conversion device, such as a laser diode, for converting electric signals into optical signals. The photoelectric conversion device 211 then converts the received optical signals into electric signals. Further, the converted electric signals may be transmitted at a speed of 500 Mbps, for example. Since the electric signals output from the photoelectric conversion device 211 are very weak, the preamplifier 212 amplifies such weak signals. The limiting amplifier 213 further amplifies signals amplified by the preamplifier 212 so as to obtain signals with a predetermined amplitude.

The clock generator 220 generates clock signals synchronized with clock signals included in the optical signals received by the photoelectric conversion device 211. The generated clock signals are used for synchronizing operation timings of correction units which will be described later with the optical signals.

The bias voltage control unit 230 includes a bias voltage level monitor 231, a bias level correction section 232, and an alarm device 233. The bias voltage level monitor 231 monitors a bias voltage level of the preamplifier 212. In addition, the bias level correction section 232 applies a positive feedback to a bias circuit of the preamplifier 212 when the monitored bias voltage level is lower than a predetermined bias threshold. Accordingly, the bias voltage level is kept to be a normal operation level. Also when the monitored bias voltage level is lower than the predetermined bias threshold, the alarm device 233 generates warning signals for an audible alarm, a warning light, a warning display, and/or the like.

Similar to the bias voltage control unit 230, the amplitude voltage control unit 240 includes an amplitude voltage level monitor 241, an amplitude level correction section 242, and an alarm device 243. The amplitude voltage level monitor 241 monitors an amplitude voltage level of an input of the limiting amplifier 213. Also, the amplitude level correction section 242 applies a positive feedback to the input of the limiting amplifier 213 when the monitored amplitude voltage level is lower than a predetermined amplitude threshold. Accordingly, the amplitude voltage level of the input of the limiting amplifier 213 is kept to be a normal operation level. Also, when the monitored amplitude voltage level is lower than the predetermined amplitude threshold, the alarm device 243 generates warning signals for an audible alarm, a warning display, and/or the like.

Exemplary basic operations of the photo receiving unit 210 are as follows. The photoelectric conversion device 211 receives optical signals transmitted from the electric-photo conversion device. When the electric-photo conversion device is provided in the transmission system of the rotation part 202, the photoelectric conversion device 211 is in the reception system of the fixed part 201. On the other hand, when the electric-photo conversion device is provided in the transmission system of the fixed part 201, the photoelectric conversion device 211 is in the reception system of the rotation part 202.

The received optical signals are then converted to electric signals in the photoelectric conversion device 211. The converted electric signals are amplified in the preamplifier 212, and the amplified electric signals are further amplified in the limiting amplifier 213 so as to have a predetermined level. The signals amplified in the limiting amplifier 213 are provided to the following units.

The preamplifier 212 and the limiting amplifier 213 will deteriorate after being used a period of time so that they cannot keep their normal characteristics or normal operations. When such deterioration occurs, the above described correction is useful so as to keep a predetermined amplifying level of the preamplifier 212 and/or a predetermined amplifying level of the limiting amplifier 213, for the time being, as a result of the monitoring. Simultaneously, when such deterioration occurs, the user of the CT apparatus 1, such as a radiological technologist, is informed of the deterioration by the alarm device 233 (243). With the above described correction, a current examination being performed by the CT apparatus 1 will be completed without any problem. This functions as a first aid until a proper fix is implemented in a maintenance service.

Figure 22:
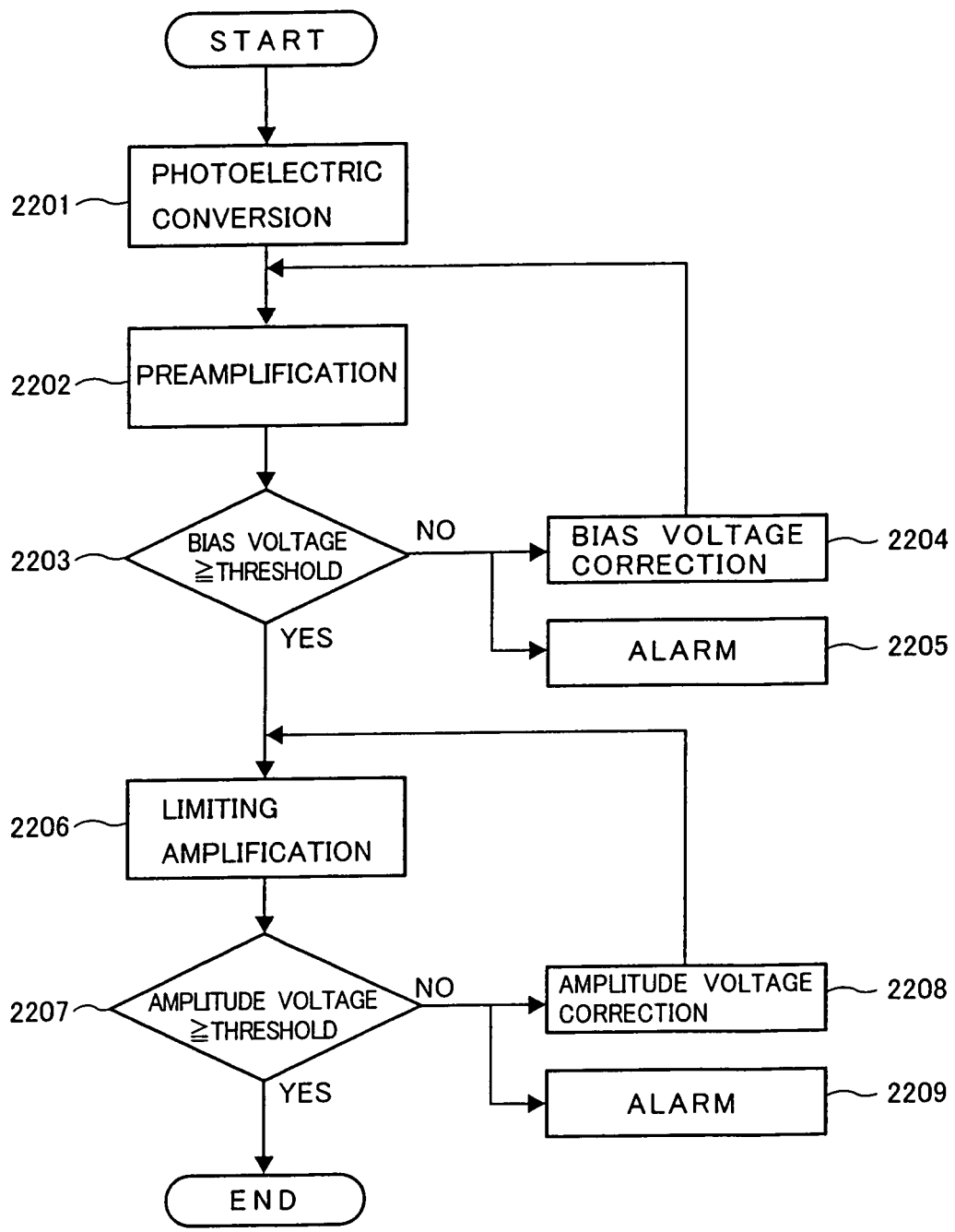
FIG. 22 is a flowchart showing a exemplary operation of the CT apparatus according to the eleventh embodiment of the present invention.

Next, detailed operations of the CT apparatus 1 will be described with reference to FIG. 22. FIG. 22 is a flowchart showing a exemplary operation of the CT apparatus 1 according to the eleventh embodiment of the present invention.

As described above, optical signals transmitted from the electric-photo conversion device or the like are received by the photoelectric conversion device 211. The received optical signals are converted into electric signals in the photoelectric conversion device 211 (step 2201). Further, the converted signals are provided to and amplified by the preamplifier 212 (step 2202). A bias voltage level of the preamplifier 212 is constantly monitored by the bias voltage level monitor 231, and the monitored bias voltage level is compared to a predetermined bias threshold (step 2203). When the monitored bias voltage level is lower than the predetermined bias threshold as a result of the comparison in step 2203, the bias level correction section 232 applies a positive feedback to a bias circuit of the preamplifier 212 so that the bias voltage level is kept at a normal operation level (step 2204). Also when the monitored bias voltage level is lower than the predetermined bias threshold, the alarm device 233 generates the warning signals (step 2205).

When the monitored bias voltage level is equal to or greater than the predetermined bias threshold, the bias voltage level correction is not made by the bias level correction section 232. By repeating the above correction when it is needed, subsequent converted signals may be amplified by the preamplifier 212 with a bias voltage level equal to or greater than the predetermined bias threshold.

The signals amplified by the preamplifier 212 are provided to and amplified by the limiting amplifier 213 (step 2206). An amplitude voltage level of an input of the limiting amplifier 213 is constantly monitored by the amplitude voltage level monitor 241, and the monitored amplitude voltage level is compared to a predetermined amplitude threshold (step 2207).

When the monitored amplitude voltage level is lower than the predetermined amplitude threshold as a result of the comparison in step 2207, the amplitude level correction section 242 applies a positive feedback to the input of the limiting amplifier 213 so that the amplitude voltage level is kept at a normal operation level (step 2208). Also when the monitored amplitude voltage level is lower than the predetermined amplitude threshold, the alarm device 243 generates the warning signals (step 2209).

When the monitored amplitude voltage level is equal to or greater than the predetermined amplitude threshold, the amplitude voltage level correction is not made by the amplitude level correction section 242. By repeating the above correction when it is needed, subsequent signals amplified in the preamplifier 212 may be amplified by the limiting amplifier 213 with an amplitude voltage level equal to or greater than the predetermined amplitude threshold. This results in providing the following units with signals having a predetermined level.

In the above operations, the signals converted by the photoelectric conversion device 211 are synchronized with predetermined clock signals. Therefore, it is necessary to synchronize a timing of signals to be corrected by the bias level correction section 232 and a timing of signals to be corrected by the amplitude level correction section 242 with the predetermined clock signals. Since transmitted signals include their clock signals, the clock generator 220 generates clock signals synchronized with the clock signals included in the optical signals received by the photoelectric conversion device 211. The generated clock signals are supplied to the bias level correction section 232 and the amplitude level correction section 242 so as to synchronize their operations timings.

According to the eleventh embodiment of the present invention, it is possible to know, at an early stage, about deterioration of characteristics of active devices due to aging. The active devices are, for example, devices included in the amplifying unit, such as the preamplifier 212 and the limiting amplifier 213. Since an alarm is issued when a characteristic has become below a predetermined threshold, it is possible to request the maintenance personnel in the local maintenance provider E to implement necessary actions, such as replacing or fixing the device, immediately. From another point of view, until such necessary actions, the CT apparatus 1 may be able to maintain a normal performance as a first aid since the bias voltage level and/or the amplitude voltage level are kept to be normal operation levels by the bias voltage control unit 230 and/or the amplitude voltage control unit 240. Therefore, at least a current radiography can be completed even if the deterioration occurs during the radiography. The specimen can also avoid unnecessary X-ray exposure which would be caused by reradiography.

When there is two or more amplifying units, an alarm device included in each of the units may have an LED (light emitting diode) and the LED may be lit when a monitored voltage level is lower than a predetermined threshold. This may make it easier for the maintenance personnel to identify which unit to fix. All of the LEDs may be centralized in the console unit 193 in a distinguishable manner so that the maintenance personnel can identify which unit to fix more quickly (at a glance). Such identification leads to identifying what is wrong or what needs to be done.

The features described above may also be applied to other types of units than the amplifying units. In addition, the amplifying units and/or the other types of units are not limited to a part of the CT apparatus 1, but may also be a part of other types of equipment including, but not limited to, medical equipment, such as an X-ray diagnosis apparatus, a magnetic resonance imaging apparatus, a nuclear medical imaging apparatus, an ultrasound diagnosis apparatus, an endoscope apparatus, and the like. Further, signals to be amplified or processed in another manner are not limited to signals converted from optical signals, but may also be signals converted from a pressure, such as, for example, a hydraulic pressure and a wind pressure. Further, the signals may also be based on vibration. The signals are also not limited to what are transmitted in a non-contact manner, but are also applied to a physically connected transmission.

In addition, if there is an enough space for mounting a backup device for, for example, the preamplifier 212 and the limiting amplifier 213, such a backup device may be replaced with a currently-used device when the characteristic of the currently-used device deteriorates and has become below a predetermined threshold. This mounting may also be applied when a cost increase is allowed. The device may also be rendered normally operative in this replacement.

(Twelfth Embodiment)

Although the CT apparatus 1 described in the eleventh embodiment has a feature of trying to maintain a normal operation for itself, a better operation of the CT apparatus 1 may be realized under the management of the medical equipment management apparatus 6. A relationship between the CT apparatus 1 described in the eleventh embodiment and the medical equipment management apparatus 6 will be described with reference to FIG. 23.

Figure 23:
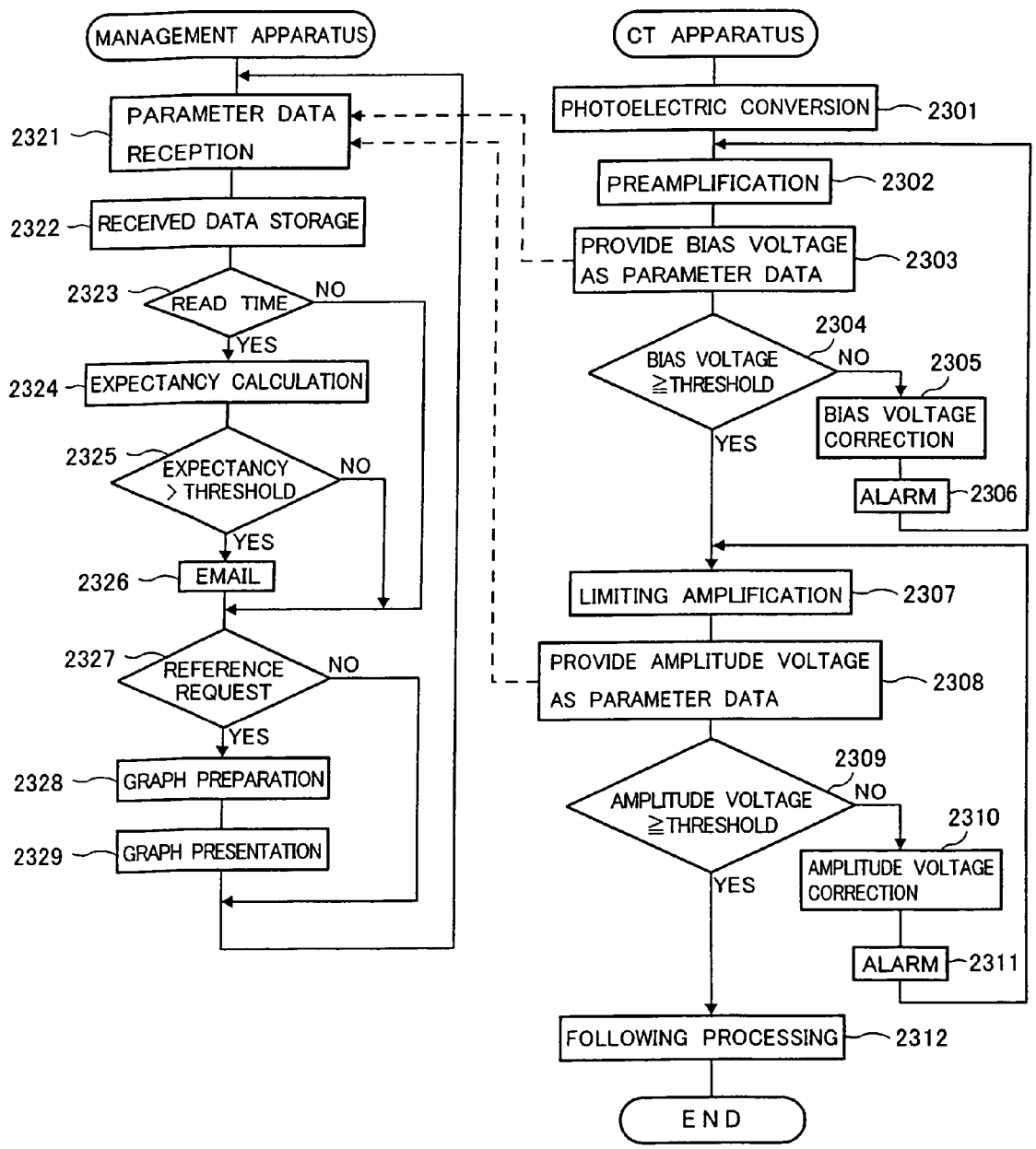
FIG. 23 is a flowchart showing a relationship between an operation flow of the CT apparatus and an operation of the medical equipment management apparatus according to a twelfth embodiment of the present invention.

FIG. 23 is a flowchart showing a relationship between an operation flow of the CT apparatus 1 and an operation of the medical equipment management apparatus 6 according to a twelfth embodiment of the present invention.

In FIG. 23, steps 2301 and 2302 correspond to the steps 2201 and 2202 in FIG. 22. Also steps 2304 to 2307 correspond to the steps 2203 to 2206 in FIG. 22. Further, steps 2309 to 2311 correspond to the steps 2207 to 2209 in FIG. 22. Still further, steps 2321 to 2329 correspond to the steps 901 to 909 in FIG. 9. Therefore, a detailed explanations of these steps is omitted.

In the CT apparatus 1, a bias voltage level of the preamplifier 212 is constantly monitored by the bias voltage level monitor 231. The monitored bias voltage level is provided to the medical equipment management apparatus 6 through the service processor 2 regularly, at any given time, or in response to a predetermined trigger event, such as requests from the medical equipment management apparatus 6 (step 2303). While provided to the medical equipment management apparatus 6, the monitored bias voltage level is also compared to a predetermined bias threshold in step 2304.

In the medical equipment management apparatus 6, the bias voltage level provided from the CT apparatus 1 is received as parameter data by the reception unit 60. Such a reception is repeated in accordance with the timing provided by the service processor 2. As a result of the repeated reception, an expectancy regarding the bias voltage level of the preamplifier 212 is predicted by calculation based on the received bias voltage levels (i.e., parameter data) in step 2324. The predicted expectancy is compared to a predetermined bias expectancy threshold in step 2325.

The predetermined bias expectancy threshold may be, but does not have to be, identical to the predetermined bias threshold. This depends on each value to be set as each of the predetermined thresholds.

Regarding an amplitude voltage level of the limiting amplifier 213 in the CT apparatus 1, it is constantly monitored by the amplitude voltage level monitor 241. The monitored amplitude voltage level is provided to the medical equipment management apparatus 6 through the service processor 2 regularly, at any given time, or in response to a predetermined trigger event, such as, for example, requests from the medical equipment management apparatus 6 (step 2308). While provided to the medical equipment management apparatus 6, the monitored amplitude voltage level is also compared to a predetermined amplitude threshold in step 2309.

In the medical equipment management apparatus 6, the amplitude voltage level provided from the CT apparatus 1 is also received as parameter data by the reception unit 60. Such a reception is repeated in accordance with the timing provided by the service processor 2. As a result of the repeated reception, an expectancy regarding the amplitude voltage level of the limiting amplifier 213 is predicted by calculation based on the received amplitude voltage levels (i.e., parameter data) in step 2324. The predicted expectancy is compared to a predetermined amplitude expectancy threshold in step 2325.

The predetermined amplitude expectancy threshold may be, but does not have to be, identical to the predetermined amplitude threshold. This depends on each value to be set as each of the predetermined thresholds.

In the medical equipment management apparatus 6, signals amplified by the limiting amplifier 213 are processed in the following units or sections (step 2312). The alarm devices 233 and 243 may not be provided or may not have to generate the warning signals in steps 2306 and 2311 if emails are transmitted to the PC 3 provided in the department of radiology in the hospital A. Further, the correction operations in steps 2304 to 2305 and/or steps 2309 to 2310 may be repeated so as to maintain a normal operation of the CT apparatus 1 even if the deterioration occurs in the preamplifier 212 and/or the limiting amplifier 213. The correction operations may continue until the maintenance service is implemented on the preamplifier 212 and/or the limiting amplifier 213 according to the email or a result of the reference request.

In the embodiments of the present invention, the medical equipment management apparatus 1 may have a random access memory (RAM), which can receive and store computer programs and applications as computer readable instructions in a temporary and/or non-volatile state. The medical equipment management apparatus may further have a hard disk drive as part of the units for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions, which when executed, may implement an embodiment of the present invention.

Accordingly, a medical equipment management apparatus which does not incorporate features of embodiments of the present invention can benefit the features as long as the medical equipment management apparatus is equipped with a feature of receiving and storing parameter data regarding a medical equipment as well as a feature of reading and performing a computer readable program.

Further, in the embodiments of the present invention described above, the probable date is only provided in response to the reference request. However, such a probable date may also be included in the email. The email may be transmitted when the probable date is within a predetermined period from a date of the determination. The email may also be transmitted in accordance with a relationship between the expectancy on the probable date and the predetermined threshold (which threshold level of the predetermined threshold).

For example, when the probable date represents a date when the expectancy becomes identical to the dangerous level of the predetermined threshold, an email including a message with information of the probable date may be transmitted to the PC 7 provided in the local maintenance provider E. The message may instruct the maintenance personnel to go to the hospital A and implement a maintenance service by one month prior to the probable date. Also when the probable date represents a date when the expectancy becomes identical to the standard level of the predetermined threshold, an email including a message with information of the probable date may be transmitted to the PC 7 provided in the local maintenance provider E. The message may instruct the maintenance personnel to implement a maintenance service in the next regular maintenance if the maintenance is scheduled by the probable date and, otherwise, to implement a maintenance service by two months prior to the probable date.

On the occasion of the expectancy prediction, there is a possibility that a parameter data has already shown a value greater than the predetermined threshold. Particularly, when a parameter data exceeds than the dangerous level, it is determined that a trouble has already occurred. It is conceivable to transmit an email instructing the maintenance personnel to go to the hospital A and fix the trouble within two hours, for example. Similarly, when a parameter data does not exceed the dangerous level but the standard level, it is determined to be a dangerous situation. It is conceivable to transmit an email instructing the maintenance personnel to go to the hospital A and fix the trouble within a few days, for example.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

The invention claimed is:

1. A medical equipment management apparatus for managing a medical equipment provided in a medical facility connected to the apparatus through a network, the apparatus comprising:
   a processor;
   a reception unit connected to the network, configured to receive parameter data from the medical equipment located in the medical facility, the parameter data is information regarding a status of a specific component of the medical equipment;
   a storage unit including a memory, connected to the network, configured to store the parameter data;
   a prediction unit connected to the network, configured to calculate an expectancy of the parameter data, which is a predicted parameter data value expected to be received in the future regarding the status of the specific component of the medical equipment, and is calculated based on the stored parameter data;
   a second reception unit connected to the network configured to receive a reference request for the expectancy from a requester;
   a providing unit connected to the network configured to allow the requester to refer to information of the expectancy based on the received reference request;

a comparison unit configured to compare the expectancy value to the first predetermined threshold level and compare the expectancy value to the second predetermined threshold level; and an informing unit configured to issue a notification message via the network to a first address when the expectancy is determined to be between the first threshold level and the second threshold level and to a second address when the expectancy is determined to exceed the second threshold.

2. The apparatus according to claim 1, wherein the informing unit is further configured to issue a notice to a local maintenance provider which provides a maintenance service for the medical equipment.

3. The apparatus according to claim 2, further comprising a second storage unit configured to store maintenance contract information of the medical equipment, and wherein the informing unit also issues the notification message to the local maintenance provider based on the stored maintenance contract information and the value.

4. The apparatus according to claim 1, wherein the informing unit issues the notification message allowing a reference of a graph which shows the stored parameter data and the expectancy with the first and second threshold levels in chronological order.

5. The apparatus according to claim 4, wherein the stored parameter data and the expectancy are shown in a distinguishable manner.

6. The apparatus according to claim 1, wherein the informing unit issues the notification message including a first content when the expectancy is determined to be between the first threshold level and the second threshold level and the notification message including a second content different from the first content when the expectancy is determined to exceed the second threshold level.

7. The apparatus according to claim 6, wherein the first content represents a necessity of a maintenance service for the medical equipment without urgency; and wherein the second content represents a necessity of an urgent maintenance service for the medical equipment.

8. The apparatus according to claim 1, wherein the parameter data represents a characteristic regarding a part of the medical equipment at each of a plurality of times.

9. The apparatus according to claim 8, wherein the parameter data is given for each of a plurality of parts of the medical equipment.

10. The apparatus according to claim 1, wherein the expectancy represents parameter data received at a predetermined time.

11. The apparatus according to claim 10, wherein the predetermined time is designated.

12. The apparatus according to claim 1, further comprising a provider configured to provide the expectancy through a telecommunication network.

13. The apparatus according to claim 12, wherein the expectancy is included in a report which reports information of the medical equipment through the telecommunication network.

14. The apparatus according to claim 12, wherein the expectancy is provided through an Internet web site.

15. The apparatus according to claim 1, further comprising a second storage unit configured to store maintenance contract information of the medical equipment.

16. The apparatus according to claim 15, wherein the stored maintenance contract information is changed by an external terminal connected to the apparatus through the network.

17. The apparatus according to claim 1, wherein the prediction unit calculates the expectancy by statistically analyzing the stored parameter data.

18. The apparatus according to claim 1,
wherein the informing unit issues the notification message including a first content when stored maintenance contract information is a first type and the expectancy is determined to exceed the second threshold level,
wherein the informing unit issues the notification message including a second content when the stored maintenance contract information is the first type and the expectancy is determined to be between the first threshold level and the second threshold level,
wherein the informing unit issues the notification message including a third content when the stored maintenance contract information is a second type and the expectancy is determined to exceed the second threshold level, and
wherein the informing unit does not issue the notification message when the stored maintenance contract information is the second type and the expectancy is determined to be between the first threshold level and the second threshold level.

19. The apparatus according to claim 1, wherein a determining condition is stored for a user of the medical equipment, and wherein a content included in the notification message is changed based on the determining condition stored for the user.

20. The apparatus according to claim 1, wherein the requester is a computer provided in a local maintenance provider which provides a maintenance service for the medical equipment.

21. The apparatus according to claim 1, wherein the requester is a computer provided in the medical facility.

22. The apparatus according to claim 1, wherein the requester is a computer provided in the apparatus.

23. The apparatus according to claim 1, wherein the information is a graph showing the stored parameter data and the expectancy.

24. The apparatus according to claim 1, wherein the prediction unit calculates the expectancy in response to the reception of the reference request.

25. The apparatus according to claim 1, wherein the prediction unit calculates the expectancy at predetermined times.

26. The apparatus according to claim 1, wherein the notification message is an e-mail.

27. The apparatus according to claim 1, wherein the predetermined data is a bias voltage level from a computed tomography apparatus.

28. A medical equipment management apparatus for managing a medical equipment provided in a medical facility connected to the apparatus through a network, the apparatus comprising:
a processor;
a reception unit connected to the network configured to receive parameter data regarding the medical equipment, the parameter data is information regarding a status of a specific component of the medical equipment;
a storage unit including a memory, connected to the network configured to store the parameter data;
a prediction unit connected to the network configured to calculate an expectancy of the parameter data, which is a predicted parameter data value expected to be received in the future regarding the status of the specific component of the medical equipment, and is calculated based on the stored parameter data;

a determination unit connected to the network configured to determine a date when the expectancy is identical to a predetermined threshold existing in the determination unit;

a second reception unit connected to the network configured to receive a reference request for the date from a computer;

a providing unit connected to the network configured to allow the computer to refer to information of the date based on the received reference request; and an informing unit configured to send a notification message over the network to a second computer according to the determined date.

29. A method of managing a medical equipment device, provided in a medical facility, the method comprising the steps of:

receiving parameter data in a reception unit connected to a network, the parameter data is information regarding a status of a specific component of the medical equipment device;

storing the parameter data in a storage unit including a memory;

calculating, using a processor, an expectancy of the parameter data to be received in the future, the expectancy is a predicted parameter data value regarding the status of the specific component of the medical equipment and is calculated based on the stored parameter data of the medical equipment device;

comparing the expectancy to a first predetermined threshold level and a second predetermined threshold level;

receiving a reference request for the expectancy from a requester;

allowing the requester to refer to information of the expectancy based on the received reference request; and issuing a notification message via the network to a first address when the expectancy is determined to be between the first threshold level and the second threshold level and to a second address when the expectancy is determined to exceed the second threshold.

30. A method of managing a medical equipment device provided in a medical facility, the method comprising the steps of:

receiving parameter data in a reception unit connected to a network, the parameter data is information regarding a status of a specific component of the medical equipment;

storing the parameter data in a storage unit including a memory;

calculating, using a processor, an expectancy, which is a predicted parameter data value expected of the parameter data to be received in the future regarding the status of the specific component of the medical equipment, and is calculated based on the stored parameter data of the medical equipment device;

receiving a reference request for the expectancy from a requester;

allowing the requester to refer to information of the expectancy based on the received reference request;

comparing the expectancy value to a first predetermined threshold level and comparing the expectancy value to a second predetermined threshold level; and issuing a notification message via a network to a first address when the expectancy is determined to be between the first threshold level and the second threshold level and to a second address when the expectancy is determined to exceed the second threshold.

31. A method of managing a medical equipment device provided in a medical facility, the method comprising the steps of:

receiving parameter data in a reception unit connected to a network, the parameter data is information regarding a status of a specific component of the medical equipment;

storing the parameter data in a storage unit including a memory;

calculating, using a processor, an expectancy, which is a predicted parameter data value expected of the parameter data to be received in the future regarding the status of the specific component of the medical equipment, and is calculated based on the stored parameter data of the medical equipment device;

determining a date when the expectancy is identical to a predetermined threshold existing in the determination unit;

receiving a reference request for the date from a computer;

providing the computer with information of the date based on the received reference request; and sending a notification message over the network to a second computer according to the determined date.

32. A management system, comprising:

a medical facility apparatus, provided in a medical facility, configured to transmit parameter data that is information regarding a status of a specific component of the medical equipment device through a network; and a medical equipment management apparatus including a processor, the medical equipment management apparatus configured to store the parameter data in a memory and to calculate an expectancy, which is a predicted parameter data value expected of the parameter data to be received in the future regarding the status of the specific component of the medical equipment, and is calculated based on the parameter data transmitted from the medical facility apparatus, to compare the expectancy value to the first predetermined threshold level and compare the expectancy value to the second predetermined threshold level, and to output a notification message indicating a situation of the medical equipment via the network to a first address when the expectancy is determined to be between the first threshold level and the second threshold level and to a second address when the expectancy is determined to exceed the second threshold, the medical equipment management apparatus also configured to receive a reference request for the expectancy from a requester.

33. A management system, comprising:

a medical facility apparatus, provided in a medical facility, configured to transmit parameter data that is information regarding a status of a specific component of the medical equipment device through a network;

a medical equipment management apparatus including a processor, the medical equipment management apparatus configured to store the parameter data in a memory and to calculate an expectancy of the parameter data, which is a predicted parameter data value expected to be received in the future regarding the status of the specific component of the medical equipment, and is calculated based on the parameter data transmitted from the medical facility apparatus, to compare the expectancy value to the first predetermined threshold level and compare the expectancy value to the second predetermined threshold level, and to transmit information of the expectancy through the network the medical equipment management apparatus also configured to receive a reference request for the expectancy from a requester; and a terminal equipment configured to receive and display the information transmitted from the medical equipment management apparatus.

34. A monitoring apparatus for managing an equipment connected to the apparatus through a network, the apparatus, comprising:

a processor;

a reception unit connected to the network configured to receive data from the equipment a plurality of times, the data is information regarding the status of a specific component of the equipment;

a storage unit including a memory, connected to the network configured to store the data;

a prediction unit connected to the network configured to calculate an expectancy of the predicted data to be received in the future regarding the status of the specific component of the medical equipment, and the expectancy is calculated based on the stored data;

a determination unit connected to the network configured to determine a date when the expectancy is identical to a predetermined threshold existing in the determination unit;

a second reception unit connected to the network configured to receive a reference request for the expectancy from a requester;

a providing unit connected to the network configured to allow the requester to refer to information of the expectancy based on the received reference request;

an informing unit connected to the network configured to issue a notice through the network; and an informing unit configured to send a notification message over the network to a second computer according to the determined date.

* * * * *